United States Patent [19]
Kroll et al.

[11] Patent Number: 5,534,015
[45] Date of Patent: Jul. 9, 1996

[54] METHOD AND APPARATUS FOR GENERATING BIPHASIC WAVEFORMS IN AN IMPLANTABLE DEFIBRILLATOR

[75] Inventors: Mark W. Kroll, Minnetonka; James E. Brewer, Maplewood, both of Minn.

[73] Assignee: Angeion Corporation, Plymouth, Minn.

[21] Appl. No.: 321,540

[22] Filed: Oct. 11, 1994

Related U.S. Application Data

[63] Continuation-in-part of Ser. No. 132,634, Oct. 6, 1993, and Ser. No. 835,836, Feb. 19, 1992, Pat. No. 5,431,686, and Ser. No. 246,007, May 19, 1994.

[51] Int. Cl.⁶ .................................................. A61N 1/39
[52] U.S. Cl. .................................... 607/7; 607/5; 607/74
[58] Field of Search .............................. 607/5, 4, 7, 74, 607/8

[56] References Cited

U.S. PATENT DOCUMENTS

| | | |
|---|---|---|
| 4,638,397 | 1/1987 | Jones et al. . |
| 4,821,723 | 4/1989 | Baker, Jr. et al. . |
| 4,850,357 | 7/1989 | Bach . |
| 4,998,531 | 3/1991 | Bocchi et al. . |
| 5,163,427 | 11/1992 | Keimel . |
| 5,230,336 | 7/1993 | Fain et al. .................... 607/7 |
| 5,468,254 | 11/1995 | Hahn et al. .................... 607/5 |

FOREIGN PATENT DOCUMENTS

| | | | |
|---|---|---|---|
| 0280526 | 8/1988 | WIPO | .................... 607/5 |
| 93/03249 | 7/1993 | WIPO | . |

OTHER PUBLICATIONS

Kroll M. W. et al., Decline in Defibrillation Thresholds, PACE 1993; 16#1:213–217.

Bardy, G. H. et al. A Prospective Fandomized Evaluation of Biphasic vs. Monophasic Waveform Pulses on Defibrillation Efficiency in Humans, J. American College of Cardiology, 1989 14:728–733.

Wyse, D. G. et al., Comparison of Biphasic and Monophasic Shocks for Defibrillation using a Non–Thoracotomy System, American J. Cardiology 1993;71:197–202.

Schuder, J. C. et al. Transthoracic Ventricular Defibrillation with Square–Wave Stimuli: One–Half Cycle, One Cycle and MultiCycle Waveforms, Circulation Research, 1964; 15:258–264.

Kavanagh, K. M. et al., Comparison of the Internal Defibrillation Thresholds for Monophasic and Double and Single Capacitor Biphasic Waveforms, J. American College of Cardiology, 1989; 14:1343–1349.

Freeser, S. A. et al., Strength–Duration and Probability of Success Curves for Defibrillation with Biphasic Waveforms, Circulation, 1990; 82:2128–2141.

Walker R. G., Walcott G. P., Swanson D. K. et al., Relationship of Charge Distribution between Phases in Biphasic Waveforms, Circulation 1992; 86 No. 4:1–792 (Abstract).

(List continued on next page.)

Primary Examiner—William E. Kamm
Assistant Examiner—Kennedy J. Schaetzle
Attorney, Agent, or Firm—Patterson & Keogh

[57] ABSTRACT

An implantable defibrillator system for generating biphasic waveforms comprises a self-contained human implantable housing containing a capacitor system for storing an electrical charge, a power supply for charging the capacitor system, and a controller for selectively discharging the electrical charge as a biphasic countershock to be delivered through at least two electrodes in response to a sensing of a cardiac dysrhythmia in the human patient. The controller includes a system for controlling a first duration of a first phase of the biphasic countershock such that the discharge of the electrical charge is of a first polarity and the first duration is variable and a system for controlling a second duration of a second phase of the biphasic countershock such that the discharge of the electrical charge is of a second polarity that is opposite from the first polarity and the second duration is fixed.

30 Claims, 6 Drawing Sheets

OTHER PUBLICATIONS

Gurvish H. L., Markarychev, V. A.: Defibrillation of the Heart with Biphasic Electrical Impulses, Kardiologilia 1967;7:109–112.

Tchou P., Krum D., Aktar M. Avitall B., Reduction of Defibrillation Energy Requirements with new Biphasic Waveforms, PACE 1990; 13:507 (Abstract).

Jones J. L., Jones R. E., Balasky G., Improved Cardiac Cell Excitation with Symmetrical Biphasic Defibrillator Waveforms, American J. Physiology 1987; 253:H1418–H1424.

Kavanagh K. M., Duff H. J., Clark R., et al., Monophasic vs. Biphasic Cardiac Stimulation: Mechanism of Decreased Energy Requirements, PACE 1990:13;1268–1276.

Swartz J. F., Jones J. L., Jones R. E., Fletcher R. D., Conditioning Prepulse of Biphasic Defibrillator Waveforms Enhances Refractoriness to Fibrillation Wavefronts, Circulation Research 1991;68:438–449.

Karasik P., Jones R., Jones J., Effect of Waveform Duration on Refractory Period Extension Produced by Monophasic and Biphasic Defibrillator Waveforms, PACE 1991;14:715 (abstract).

Tang ASL, Yabe S., Wharton J. M. et al., Ventricular Defibrillation Using Biphasic Waveforms: The Importance of Phasic Defibrillation, J. American College of Cardiology 1989; 13:207–14.

Bourland J. D., Tacker W. A., Geddes L. A. et al., "Comparative Efficacy of Damped Sign Wave and Square Wave current for Transchest Ventricular Defibrillation in Animals", Medical Instrumentation 1978;12#1:38–41.

Irnich W., "The Chronaxie Time and its Practical Importance", PACE 1980;8:870–888.

Kroll M. W., Adams T. P., "The Optimum Pulse Width for the Implantable Defibrillator", 7th Purdue Conference on Defibrillation, American Heart Journal 1992;124#3;835.

Schwartz J. F., Karasik P. E., Donofrio J. et al., "Effect of Biphasic Waveform Tilt on Human Non–Thoracotomy Defibrillation Threshold", PACE 1993;16#4II:888.

Ideker R. E., Tang A. S. L., Frazier D. W. et al., "Ventricular Defibrillation: Basic Cocepts:, Cardiac Pacing and Electophysiology"3rd Ed., edited by El–Sherif N. & Samatt, W. B. Saunders Co. Philadelphia 1991;42:713–726.

Frazier D. W., Wolf P. D., Wharton J. M., et al., "A Stimulas Induced Critical Point: A Mechanism for Electrical Initiation of Re–Entry in Normal Canine Myocardium", J. of Clinical Investigation 1989;83:1039.

Shibata N., Chen P. S., Dixon E. G., et al., "Epicardial Activation After Unsuccessful Defibriallation Shocks in Dogs", American J. Physiology 1988;255:H902–H909.

Zhou X. Daubert J. P., Wolf P. D., et al., "Epicardial Mapping of Ventricular Defibrillation with Monophasic and Biphasic Shocks in Dogs":, Circulation Research 1993;72:145–160.

Jones J L, Jones R. E., "Decreased Defibrillator–Induced Dysfunction with Biphasic Rectangular Waveforms", American J. Physiology 1984:247:H792–796.

Niebauer M. J., Babbbs C. F., Geddes L. A., et al., "Efficacy and Safety of the Reciprocal Pulse Defibrillator Current Waveform", Medical and Biological Engineering and Computing 1984;22:28–31.

Kavanagh, K. M. et al., Comparison of the Internal Defibrillation Thresholds for Monophasic and Double and Single Capacitor Biphasic Waveforms, J. American College of Cardiology, 1989;14:1343–1349.

Feeser S. A., Tang A. S. L., Kavanagh K. M., et al., "Strength—Duration and Probability of Success Curves for Defibrillaion with Biphasic Waveforms" Circulation 1990;82:2128–2141.

Dixon E. F., "Improved Defibrillaion Thresholds with Large Contoured Epicardial Electrodes and Biphasic Waveforms", Circulation, 1987;76:1176–1184.

Chapman, et al., "Efficacy of Monophasic and Biphasic Truncated Exponential Shocks for Nonthoracotomy Internal Defibrillation in Dogs", J. American College of Cardiology, 1988;12:739–745.

Dillon S. M., "Synchronized Depolarized after Defibrillation Shocks: A Possible Component of the Defibrillation Process Demonstrated by Optical Recordings in Rabbit Heart", Circulation 1992;85:1865–1878.

Sweeney R. J., et al., "Ventricular Refractory Period Extension Caused by Defibrillation Shocks", Circulation 1990;82:965–972.

Belz M. K. et al., "Successful Defibrillation Prolongs Action Potential Durations in Humans", PACE 993;16:932.

Frasier D. W. et al., "Extracellular Field Required for Excitation in Three–Dimensional Anisotropic Canine Myocardium":, Circulation Research 1988;63:147–164.

Wessale J. L. et al., "Bipolar Catheter Defibrillation in Dogs using trapezoidal Waveforms of Various Tilts", J. Electrocardiology 1980;13(4):359–366.

Wharton J. M. et al., "Electrophysiological Effects in Vivo Monophasic and Biphasic Stimuli in Normal and Ifarcted Dogs", PACE 1990;13:1158–1172.

Niebauer M. J., Babbbs C. F., Geddes L. A., et al., "Efficacy and Safety of Defibrillation with Rectangular Waves of 2 to 20–milliseconds Duration", Crit. Care Medicine 1983;11#2:95–98.

Daubert J. P. et al., "Response of Relatively Refractory Canine Myocardium to Monophasic and Biphasic Shocks", Circulation 1991;84:2522–2538.

Zhou X. Daubert J. P., Wolf P. D., et al., "Prolongation of Repolarization Time by Electric Field Stimulation with Monophasic and Biphasic Shocks in Open Chest Dogs", Circulation Research 1991;68:1761–1767.

Yabe S., et al., "Conduction Disturbances Caused by High Current Density Electric Fields", Circulation Research 1990;66:1190–1203.

Fozzard H. A., "Membrane Capacity of the Cardiac Purkinje Fiber", J. physiol (Great Britian) 1966;182:255–267.

Weidmann S., "Electrical Constants of Trabecular Muscle from Mammalian Heart", J. Physiol (Great Britian) 1970;210:1041–1054.

Knisley S. B. et al., "Optical Measurement of Transmembrance Potential Changes During Electric Field Stimulation of Ventricular Cells", Circulation Research 1993;72:255–270.

January C. T. et al., "Early After Depolarization Newer Insights into Cellular Mechanisms":, J. Cardiovascular Electrophysiology 1990;1:161–169.

Shibata N. et al., "Epicardial Activation After Unsuccessful Defibrillation Shocks in Dogs", American J. Physiology 1988;255:H902–909.

Chen P. S. et al., "Epicardial Activation During Ventricular Defibrillation in Open–Chest Dogs", J. Clinical Investigation 1986;77:810'823.

Cooley J. W., Dodge F. A., "Digital Computer Solutions for Excitation and Propagation of the Nerve Impulse", Biophysical Journal 1966;6:583–599.

Krassowska W., et al., "Propagation vs. Delayed Activation During Field Stimulation of Cardiac Muscle", PACE 1992;15:197–210.

Schwartzman D. et al., "Serial Patch—Patch Impedence Values in an Epicardial Defibrillation System", PACE 1993;16:916.

Cooper R. et al., "The Effect of Phase Separation on Biphasic Waveform Defibrillation", PACE, vol. 6, Mar., Part I, 1993.

Kao C. Y., Hoffman B. F., "Graded and Decremental Response in Heart Muscle Fiber", American J. Physiology 1958;194(1):187–196.

J L Prevost and F Batelli "Sur quelques effects des descharges electriques sur le cover des mammifers," Comples rendus hebdomadaires des seances del Academie des sciences, vol. 129, pp. 1267, 1899.

AC Guyton & J Satterfield, "Factors concerned in defibrillation of the heart, particularly through the unopened chest," Am. J. of Physiology, vol. 167, pp. 81, 1951.

J C Schuder, et al. "Transthoracic ventricular defibrillation with triangular and trapezoidal waveforms," Cir. Res. vol. 19, pp. 689–694, Oct., 1966.

W A Tacker et al., "Optimum current duration for capacitor-discharge defibrillation of canine ventricles," J. Applied Physiology, vol. 27#4, pp. 480–483, Oct. 1969.

J C Schuder et al., "Transthoracic ventricular defibrillation in the dog with truncated and untruncated exponential stimuli," IEEE Trans. Blom. Eng., vol. BME 18#6, pp. 410–415, Nov. 1971.

6 Weiss, "Sur la possibilité de rendre comparable entre eux les appareils survant a l'excitation electique, " Arch. Ital. de Biol., vol. 35, p. 413–446, 1901.

J D Bouriand et al., "Strength duration curves for trapezoidal waveforms of various tilts for transchest defibrillation in animals,"Med. Instr., vol. 12#1, pp. 38–41, 1978.

L Lapicque "Definition experimentalle de excitable," Proc. Soc. de Biol., vol. 77, pp. 280–285, 1909.

P S Chen et al., "The potential gradiant field created by epicardial defibrillation electrodes in dogs, " Circulation, vol. 74, pp. 626–635, Sep. 1986.

M Mirowski et al., "Stand by automatic defibrillator," Arch Int Med., vol. 126 pp. 158–161, Jul. 1970.

J C Schuder et al., "Ventricular defibrillation in the dog with a bielectrode intravascular catheter", Arch. Int. Med., vol. 132 pp. 286–290, Aug. 1973.

M Mirowski et al., "Feasibility and effectiveness of Ion–energy catheter defibrillation in man," Circulation, vol. 47, pp. 79–85, Jan. 1973.

Kroll, M W et al., "A Quantitative Model of the Biphasic Defibrillation Waveform," PACE, vol. 16, No 9, p. 1923 (Abstract).

M W Kroll, "A Minimal Model of the Monophasic Defibrillation Pulse," PACE, vol. 16, pp. 769–777; Apr. 1993.

D L Lang et al., "Strength–Duration Relationship for Biphasic Defibrillation in Dogs," IEEE Eng. in Med. & Biol. Soc. 11th Annual Int. Conf., pp. 80–81, 1989.

METHOD AND APPARATUS FOR GENERATING BIPHASIC WAVEFORMS IN AN IMPLANTABLE DEFIBRILLATOR

RELATED APPLICATIONS

This application is a continuation-in-part application of three co-pending applications previously filed in the United States Patent and Trademark Office, the first of which was filed on Oct. 6, 1993 and entitled METHOD AND APPARATUS FOR GENERATING BIPHASIC WAVEFORMS IN AN IMPLANTABLE DEFIBRILLATOR, Ser. No. 08/132,634, the second of which was filed on Feb. 19, 1992 and entitled "OPTIMAL PULSE DEFIBRILLATOR", Ser. No. 07/835,836, now U.S. Pat. No. 5,431,686, and the third of which was filed on May 19, 1994 and entitled "AN IMPLANTABLE DEFIBRILLATOR SYSTEM FOR GENERATING AN ACTIVE BIPHASIC WAVEFORM", Ser. No. 08/246,007, all of which are assigned to the assignee of the present invention and the disclosure of each of which is hereby incorporated in the present application.

This application is also related to a co-pending application filed in the United States Patent and Trademark Office on Mar. 15, 1993 and entitled IMPLANTABLE CARDIOVERTER DEFIBRILLATOR HAVING A SMALLER DISPLACEMENT VOLUME, Ser. No. 08/033,632, which is assigned to the assignee of the present invention and the disclosure of which is hereby incorporated in the present application.

BACKGROUND OF THE INVENTION

1. Field of the Invention

The present invention relates generally to implantable defibrillator systems, and more particularly, to a method and apparatus for generating biphasic waveforms with an implantable defibrillator system.

2. Background of the Invention

Implantable defibrillator systems deliver a high voltage electrical countershock to the heart in an attempt to correct or convert a detected cardiac arrhythmia or fibrillation. Due to the limitations on size and power imposed by the fact that these systems must be self-contained implantable devices, all existing implantable defibrillator systems generate an electrical countershock by charging a capacitor system to a high voltage. The electrical charge stored in the capacitor system is then delivered as a truncated capacitive discharge through two or more implanted electrodes.

To date, there have been two basic kinds of truncated capacitive discharge waveforms which have been used with implantable defibrillator systems: monophasic waveforms and biphasic waveforms. Monophasic waveforms are comprised of a single monotonically decaying electrical pulse that is typically truncated before the capacitor system is completely discharged. Biphasic waveforms, on the other hand, are comprised of a pair of decaying electrical pulses or phases that are of opposite polarity. To generate a biphasic pulse, a first pulse or phase is discharged from the capacitor system in the same manner as a monophasic waveform and then, at the point the first pulse is truncated, an H-bridge switch circuit connected to the electrodes is used to immediately reverse the discharge polarity of the capacitor system as seen by the electrodes in order to produce the second pulse or phase of the biphasic waveform that is of the opposite polarity. A typical example of the use of an H-bridge circuit to generate a biphasic waveform in an implantable defibrillator system is shown in U.S. Pat. No. 4,998,531.

Over the last twenty five years, it has been demonstrated that appropriately truncated biphasic waveforms can achieve defibrillation with significantly lower currents, voltages and energies than monophasic waveforms of similar durations. Kroll, MW et al., "Decline in Defibrillation Thresholds", *PACE* 1993; 16#1:213–217; Bardy, GH et al., "A Prospective Randomized Evaluation of Biphasic vs. Monophasic Waveform Pulses on Defibrillation Efficiency in Humans", *J American College of Cardiology*, 1989; 14:728–733; and Wyse, DG et al., "Comparison of Biphasic and Monophasic Shocks for Defibrillation using a Non-Thoracotomy System", *American J Cardiology* 1993; 71:197–202. These findings are of particular importance for implantable devices because of the direct relationship between the amount of energy required for defibrillation and the overall size of the implantable device, i.e., the lower the energy required for defibrillation, the smaller the device.

Numerous theories have been advanced to explain the improved efficiency of the biphasic waveform over the more conventional monophasic waveform. Several of these theories may be relevant and may in fact act jointly. To date, the following general theories have been advanced in the literature: (1) zero net charge transfer; (2) current summing; (3) sodium channel reactivation; (4) shortening of the refractory period; (5) lowering of the impedance; (6) improved energy delivery; and (7) change in the critical point. As a background, each of these theories will be briefly summarized to contrast them with the theory employed by the present invention.

(1) Zero Net Charge Transfer—The first paper on the biphasic defibrillation waveform was arguably presented by Schuder in 1964. In that paper he observed, "an important feature of the one-cycle bi-directional shock is that, despite the arbitrary starting point, the net electrical charge transport is zero." Schuder JC, Stoeckle EH, Dolan AM, "Transthoracic Ventricular Defibrillation with Square-Wave Stimuli: One-Half Cycle, One Cycle, and MultiCycle Waveforms", *Circulation Research* 1964;15:258–264. However, a recent study found a negative correlation between the charge contents in each phase of efficient biphasic shocks of a certain design. Walker RG, Walcott GP, Swanson DK, et.al., "Relationship of Charge Distribution between Phases in Biphasic Waveforms", *Circulation 1992;86* No.4:I-792. (Abstract). This would imply that a zero net charge transfer was not required or necessarily efficient, and that a zero net charge transfer (at least at the electrode level) may not be important for the efficacy of a biphasic waveform.

(2) Current Summing—It has also been suggested that when the second phase of a biphasic pulse is removed, thereby creating a monophasic pulse, it is necessary to increase the discharge voltage of this pulse so that the current amplitude would be equal to the sum of current values of 2 first half periods for the discharge. Consequently, the capacity of the heart to summate the stimulation effect of both phases of current may be utilized for reduction of the defibrillating current in one direction and for decreasing the hazard of the heart injury by a strong current. Gurvish NL, Markarychev, VA: "Defibrillation of the Heart with Biphasic Electrical Impulses", *Kardiologilia* 1967;7:109–112. A similar result was found more recently suggesting that the total voltage change from the trailing edge of the first phase to the leading edge of the second phase was an important factor in the defibrillation pulse. Tchou P, Krum D, Aktar M, Avitall B, "Reduction of Defibrillation Energy Requirements with new Biphasic Waveforms", *PACE* 1990; 13:507. (Abstract)

The summing hypothesis is tempting in that the sum of the currents (or voltages) in the two phases of a biphasic shock is indeed comparable to the current in a monophasic shock of similar efficacy. However, this theory does not explain the sensitivity of the biphasic efficiency to the duration of the second phase.

(3) Reactivation of the Sodium Channels—It has been suggested that the first phase of the biphasic waveform serves as a conditioning prepulse which helps to restore sodium channel activation in preparation for the excitation by the second phase. Jones JL, Jones RE, Balasky G, "Improved Cardiac Cell Excitation with Symmetrical Biphasic Defibrillator Waveforms", *American J Physiology* 1987;253:H1418-H1424. This reactivation hypothesis was given additional support and a theoretical underpinning in a later paper which demonstrated that a hyperpolarizing prepulse did reactivate additional sodium channels thus promoting increased excitability. Kavanagh KM, Duff HJ, Clark R, et.al., "Monophasic vs. Biphasic Cardiac Stimulation: Mechanism of Decreased Energy Requirements", *PACE* 1990:13;1268–1276. This theory may explain why the biphasic wave prolong refractoriness after the shock. Swartz JF, Jones JL, Jones RE, Fletcher RD, "Conditioning Prepulse of Biphasic Defibrillator Waveforms Enhances Refractoriness to Fibrillation Wavefronts", *Circulation Research* 1991;68:438–449. Unfortunately, this enhanced stimulation effect is very dependent on waveform duration. Karasik P, Jones R, Jones J., "Effect of Waveform Duration on Refractory Period Extension Produced by Monophasic and Biphasic Defibrillator Waveforms", *PACE* 1991;14:715. (Abstract). Thus, the reactivation theory for biphasic waveforms may or may not be important depending upon the importance of the extension of refractory period vs. synchronization as the fundamental basis of defibrillation.

(4) First Phase Shortening of Refractory Period—It has been long known that a hyperpolarizing pulse delivered during phase 2 of the action potential can shorten the refractory period, thus, allowing a depolarizing pulse to more easily activate the cell, and it has been suggested that this mechanism could explain the increased effectiveness of the biphasic shock. Tang ASL, Yabe S, Wharton JM, et.al., "Ventricular Defibrillation Using Biphasic Waveforms: The Importance of Phasic Defibrillation", *J American College of Cardiology* 1989;13:207–14. This proposed theory is similar to the sodium channel reactivation hypothesis and the cited literature may apply in both cases.

(5) Lower Impedance—There is some evidence that the average current of a pulse is the best measure of its effectiveness (for a given pulse duration). Bourland JD, Tacker WA, Geddes LA. et al., "Comparative Efficacy of Damped Sign Wave and Square Wave Current for Transchest Ventricular Defibrillation in Animals", *Medical Instrumentation* 1978;12#1:38–41. Thus, for a given voltage in a waveform, one would expect that the waveform with the lowest impedance would be the most efficacious. It has been found that the average impedance of the second phase of a biphasic waveform is significantly lower than that of the first phase. Tang ASL, Yabe S, Wharton JM, et.al., "Ventricular Defibrillation Using Biphasic Waveforms: The Importance of Phasic Defibrillation", *J American College of Cardiology* 1989;13:207–14. The lower impedance theory, however, is suspect for two reasons. First, the reductions in required voltage are found to be lower than the impedance reductions and, as a result, the current requirement is itself reduced for the biphasic waveform. Second, the impedance reduction results from the transition between the phases and thus only benefits the second phase of the shock. As a result, the lower impedance theory does not explain the overall improvements in efficacy which have been observed for the biphasic waveform.

(6) Improved Energy Delivery—It has been suggested that the increased efficacy of the biphasic waveform is due to its ability to deliver a larger fraction of the energy in the capacitor for a typical capacitive discharge defibrillator. U.S. Pat. No. 4,850,357, issued to Bach and entitled "Biphasic Pulse Generator for an Implantable Defibrillator". Clearly one could deliver more of the energy in a capacitor by merely increasing the duration of the pulse, but this has been shown to be deleterious in that long durations can lower the average current and thereby decrease efficiency. Kroll MW, Adams TP, "The Optimum Pulse Width for the Implantable Defibrillator", 7th Purdue Conference on Defibrillation, *American Heart Journal* 1992;124#3: 835. (Abstract).

For general stimulation and defibrillation, it has been shown that pulses significantly wider than the appropriate chronaxie time use energy inefficiently. Irnich W, "The Chronaxie Time and its Practical Importance", *PACE* 1980;8:870–888. By delivering the energy in two shorter phases, one could utilize the energy without the penalty of the increased duration. A reasonably efficient capacitive discharge monophasic waveform will deliver nearly 90% of the capacitor's energy with an efficient pulse duration. By use of the biphasic waveform one can thus deliver another 10% of the energy. However the energy reductions reported, for biphasic usage, are significantly greater than 10%. It has also been shown that, for a more optimal duration, the stored energy requirements were also lowered with the biphasic waveform. Swartz JF, Karasik PE, Donofrio J, et.al., "Effect of Biphasic Waveform Tilt on Human Non-Thoracotomy Defibrillation Threshold", *PACE* 1993;16#4II:888 (Abstract). Thus, the argument that the increased benefit of biphasic waveforms might lie from increasing the percentage of energy delivered can certainly not account for all of the effects which have been observed.

(7) Differences in the Critical Point—It has been suggested that differences in the critical point of the biphasic waveform may explain its advantage over the monophasic waveform. Ideker RE, Tang ASL, Frazier DW, et.al., "Ventricular Defibrillation: Basic Concepts", *Cardiac Pacing and Electrophysiology* 3rd Ed., edited by El-Sherif N & Samatt, WB Saunders Co. Philadelphia 1991;42:713–726. Re-entry may be induced when a sufficient potential gradient exists that is at an angle (e.g., perpendicular) to the dispersion of refractoriness. This has been shown to exist with a shock field of 5 V/cm in tissue just recovering from its effective refractory period. Frazier DW, Wolf PD, Wharton JM, et.al., "A Stimulus Induced Critical Point: A Mechanism for Electrical Initiation of Re-Entry in Normal Canine Myocardium", *J of Clinical Investigation* 1989;83:1039. According to this theory, it is thought, because these potential gradients exceeding the critical value can cause unidirectional block and prolongation of refractoriness, there is a lower critical point. If the biphasic shock has a lower critical point, then there is less of a chance of refibrillation from the shock. It has been shown, however, that the first reactivation following an unsuccessful countershock is typically found in the region with the lowest gradient, not the highest. Shibata N, Chen PS, Dixon EG, et. al., "Epicardial Activation After Unsuccessful Defibrillation Shocks Dogs", *American J Physiology* 1988;255:H902-H909

Beside the experimental findings that the biphasic waveform has lower defibrillation thresholds, there are several specific findings which should be considered to better understand the nature of the difference between monophasic and biphasic waveforms. Most importantly, these experimental findings should be explainable by any putative theory of the biphasic waveform advantage. These specific findings are: (1) the biphasic wave generates fewer post shock arrhythmias; (2) a symmetric biphasic offers minimal or no benefit; (3) the second phase duration for a single capacitor shock should be shorter than the first duration; and (4) there is less benefit with the biphasic waveform for transthoracic defibrillation.

(1) Biphasic Waveform has Fewer Post Shock Arrhythmias—There are several reports that the biphasic waveform has fewer post shock arrhythmias than does the monophasic waveform for shocks of equal strength. This is certainly true for shocks near their threshold levels. This was first noted as a "distinct impression" without a statistical analysis in the early Schuder paper, and was confirmed in a recent study with dogs. Zhou X, Daubert JP, Wolf PD, et al., "Epicardial Mapping of Ventricular Defibrillation With Monophasic and Biphasic Shocks in Dogs", *Circulation Research* 1993;72:145–160. When the duration of the post shock arrhythmias is measured by detecting the contraction arrest time, it has been shown that the arrest time for rectangular biphasic waveforms with optimal durations could be reduced to half of the arrest time associated with monophasic waveforms of similar strength. Jones JL, Jones RE. Decreased Defibrillator—Induced Dysfunction with Biphasic Rectangular Waveforms. *American J Physiology* 1984;247:H792-H796.

(2) Symmetric Biphasic Offer Little or No Benefit—A study of isolated perfused canine hearts using symmetrical biphasic pulses—each phase had an identical amplitude and durations of 5 ms—showed no advantage in the threshold energy for defibrillation. Niebauer MJ, Babbs CF, Geddes LA, et.al., "Efficacy and Safety of the Reciprocal Pulse Defibrillator Current Waveform", *Medical and Biological Engineering and Computing* 1984;22:28–31. In this study, myocardial depression was defined as the percentage decrease in systolic pressure, and it was found that the symmetric biphasic waveform also offered no advantage in minimizing myocardial depression at any multiple of the defibrillation threshold current. Similar results were obtained with a "double capacitor" biphasic waveform in which a separate capacitor was used for each phase to ensure symmetry. Kavanagh KM, Tang ASL, Rollins DL, et.al., "Comparison of the Internal Defibrillation Thresholds for Monophasic and Double and Single Capacitor Biphasic Waveforms", *J American College of Cardiology* 1989;14:1343–1349. Another example that symmetric biphasic waveforms offer no advantage is a study that used a single capacitor waveform of 7 ms which had a threshold of 1.19 J, while the symmetric dual capacitor waveform with both the first and second phase each being 7 ms had a 1.99 J threshold. Feeser SA, Tang ASL, Kavanagh KM, et.al. Strength—Duration and Probability of Success Curves for Defibrillation with Biphasic Waveforms. *Circulation* 1990;82:2128–2141.

(3) Efficient Biphasic Has Phase 2 Shorter than Phase 1—In a study done with a right ventricular catheter and a subcutaneous patch in dogs, single capacitor biphasic waveforms for which the first phase was 50, 75, and 90% of the total duration had a lower defibrillation energy threshold than a monophasic waveform of the same total duration. However for waveforms in which the second phase had 75 or 90% of the total duration the energy requirements increased significantly. Chapman PD, Vetter JW, Souza JJ, et.al. "Comparative Efficacy of Monophasic and Biphasic Truncated Exponential Shocks for Nonthoracotomy Internal Defibrillation in Dogs. *J American College of Cardiology* 1988;12:739–745.

Similar results were found in dogs with epicardial patch electrodes in which a total of 25 combinations of first and second phase durations were studied. In all cases in which the second phase duration was shorter than the first phase duration, the total energy required was lower than that of a monophasic wave whose duration was equal to the first phase duration of the biphasic wave. Conversely, in all cases in which the second phase duration was greater than the first phase, the energy requirements were increased over the comparable monophasic waveform. Feeser SA, Tang ASL, Kavanagh KM, et.al., "Strength—Duration and Probability of Success Curves for Defibrillation with Biphasic Waveforms", *Circulation* 1990;82:2128–2141.

Still another canine study used both epicardial and pericardial patches found that the single capacitor biphasic waveforms with the lowest energy thresholds had a second phase shorter than the first phase. As with the other studies, those shocks with the second phase longer than the first phase had thresholds greater than that of comparable monophasic waveforms. Dixon EF, Tangas L, Wolf PD, Meador JT, Fine MG, Calfee RV, Ideker RE, "Improved Defibrillation Thresholds with Large Contoured Epicardial Electrodes and Biphasic Waveforms", *Circulation*, 1987;76:1176–1184.

(4) Biphasic Waveform Has Less Transthoracic Advantage—Another canine study compared monophasic and biphasic thresholds for both internal and external defibrillations. While the biphasic waveforms had energy thresholds that were approximately one half of those of the monophasic waveforms for internal defibrillation, the advantages of the biphasic waveform in external defibrillation, although still seen although, were usually not statistically significant when comparing waveforms of similar durations. Johnson EE, Hagler JA, Alferness CA, et al., "Efficacy of Monophasic and Biphasic Truncated Exponential Shocks for Nonthoracotomy Internal Defibrillation in Dogs", *J American College of Cardiology*, 1988;12:739–745.

Although some of these theories may partly explain, or may act cooperatively to explain, the various experimental effects which have been observed when a biphasic waveform is applied to the heart, there is currently no single accepted theory which fully explains the advantages of the biphasic waveform over the monophasic waveform. As a result, there is little or no agreement on what factors might further improve the efficiency and operation of the biphasic waveform.

This lack of agreement as to the theoretical basis for the enhanced efficacy and operation of the biphasic waveform has resulted in the use of two different techniques for generating and delivering biphasic waveforms from an implantable defibrillator. In the first technique, as described for example in U.S. Pat. No. 4,850,357 issued to Bach, Jr., each phase of the biphasic waveform is controlled by truncating the discharge of the capacitor system at a predefined tilt or percentage exponential decay as sensed by an output sensing circuit. This first technique for generating biphasic waveforms is used in the PRC® and Jewel® devices manufactured by Medtronic, Inc., as well in the PRx® and PRx II® devices manufactured by CPI, Inc. In the second technique, as described, for example in U.S. Pat. No. 4,821,723 issued to Baker et al., each phase of the biphasic waveform is controlled by truncating the discharge of the capacitor system at a predefined time interval as measured by some type of timer. This second technique for generating biphasic waveforms is used in the Cadence® device manufactured by Ventritex, Inc., as well as in the Guardian® device manufactured by Telectronics, Inc.

While existing implantable defibrillator systems are capable of generating electrical countershocks that utilize the more efficient biphasic waveform, there presently is no single accepted theory for why the biphasic waveform is more efficient. This lack of an understanding of the nature and effect of the biphasic waveform has impeded further development and enhancement of the biphasic waveform. Accordingly, it would be desirable to provide a method and apparatus for generating biphasic waveforms as a result of an improved understanding of the nature and effect of the biphasic waveform on the fibrillating myocardium.

SUMMARY OF THE INVENTION

The present invention provides a method and apparatus for generating biphasic waveforms for an implantable defibrillator. The implantable defibrillator system comprises a self-contained human implantable housing containing a capacitor system for storing an electrical charge, a power supply for charging the capacitor system, and a controller for selectively discharging the electrical charge as a biphasic countershock to be delivered through at least two electrodes in response to a sensing of a cardiac dysrhythmia in the human patient. The controller includes a system for controlling a first duration of a first phase of the biphasic countershock such that the discharge of the electrical charge is of a first polarity and the first duration is variable and a system for controlling a second duration of a second phase of the biphasic countershock such that the discharge of the electrical charge is of a second polarity that is opposite from the first polarity and the second duration is fixed.

Many theories have been offered for the improved efficacy of the biphasic defibrillation waveform. The present invention uses a unique quantitative model based on the theory that the function of the first phase of the biphasic waveform is to synchronize the myocardium as is done with a conventional monophasic wave, and the function of the second phase is to remove any residual charge from the cell membranes, which was deposited by the first phase of the shock. The model used by the present invention assumes that the effective current requirements of the first phase are a linear function of the calculated residual (after the second phase) cell membrane voltage squared. For an ICD system having a single capacitor system, the model utilized by the present invention predicts that the duration of the second phase should be a constant within the range of 2 ms to 4 ms, and preferably about 2.5 ms, for the range of presently encountered ICD capacitances and electrode resistances.

In a preferred embodiment of the present invention, the system for controlling the first duration discharges a first portion of the electrical charge based upon a measured tilt of an output voltage of the electrical charge and discharges a second portion of the electrical charge based on a predetermined time value. Ideally, this is determined by using a percentage of a system time constant for the implantable defibrillator system to determine the first portion of the discharge and using a percentage of a predetermined human chronaxie value to determine the second portion of the discharge. Alternatively, the system for controlling the first duration can dynamically measure a resistance value across the at least two electrodes that is then used to variably control the first duration for the first phase. In each of these embodiments, the implantable defibrillator system can communicate with a programming device external to the human patient to programmably establish at least one programmable value selected from the set comprising: a tilt value for the first duration, a tilt value and a fixed value for the first duration, a fixed value for the second duration and any combination thereof.

In an alternate embodiment of the present invention, the controller includes a system for controlling a first duration of a first phase of the biphasic countershock such that the discharge of the electrical charge is of a first polarity and the first duration is variable and increases with an increase of a system time constant for the implantable defibrillator system, and a system for controlling a second duration of a second phase of the biphasic countershock such that the discharge of the electrical charge is of a second polarity that is opposite from the first polarity and the second duration is variable and decreases with an increase of the system time constant for the implantable defibrillator system. This embodiment is particularly useful where the system time constant is less than about 2 milliseconds, such as when an effective capacitance of the capacitor system is less than about 80 μF and an interelectrode resistance between the at least two electrodes is greater than about 25 Ω. Preferably in this embodiment, an optimal second duration ($d_2$) is determined by solution of the equation:

$$d_2(opt) = [(\tau_s \tau_m)/(\tau_s - \tau_m)] \ln [2 - (e^{-d_1/\tau_m}/e^{-d_1/\tau_s})],$$

where ($d_1$) is the first duration of the first phase of the biphasic waveform, $\tau_s$ is the system time constant for the implantable defibrillator system and $\tau_m$ is a system time constant for a heart cell membrane.

DESCRIPTION OF THE PREFERRED EMBODIMENTS

The description of the preferred embodiments will first review the standard biphasic waveform and single capacitor system circuitry which is used to produce that waveform in existing ICD systems. With this background in mind, a new model for understanding biphasic waveforms is presented. The new model is then applied to optimize biphasic waveforms produced by single capacitor system.

Existing ICD Systems and Biphasic Waveforms

Figure 1:
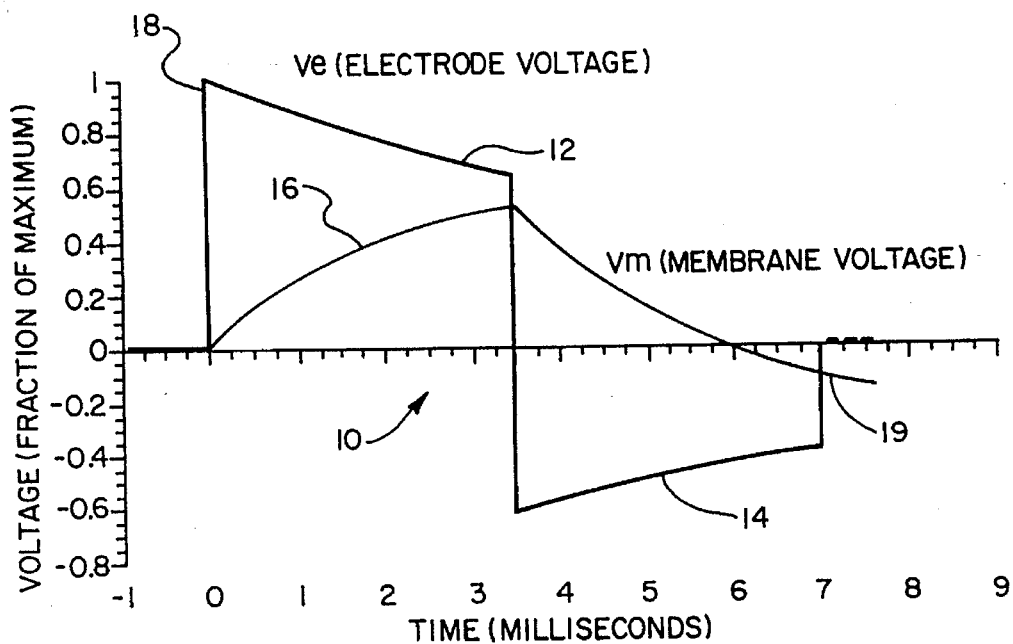
FIG. 1 shows the output voltages for a typical biphasic waveform produced by a single capacitor system implantable defibrillator.

FIG. 1 shows the output voltages of an electrical countershock for a typical biphasic waveform 10 produced by a single capacitor system implantable defibrillator. Biphasic waveform 10 consists of a first phase 12 shown as having a positive polarity and a second phase 14 shown as having a negative polarity, although it will be understood that the polarities of the phases 12 and 14 could be reversed, so long as the respective polarities of phases 12 an 14 are opposite one another. In addition to the electrode voltage for biphasic waveform 10, FIG. 1 also shows a typical myocardial cell membrane voltage 16 in response to the delivery of the electrical countershock. For ease of representation, the voltages shown in FIG. 1 are shown as normalized voltages expressed in arbitrary percentage units of the initial charging voltage 18 of the single capacitor system.

Figure 2:
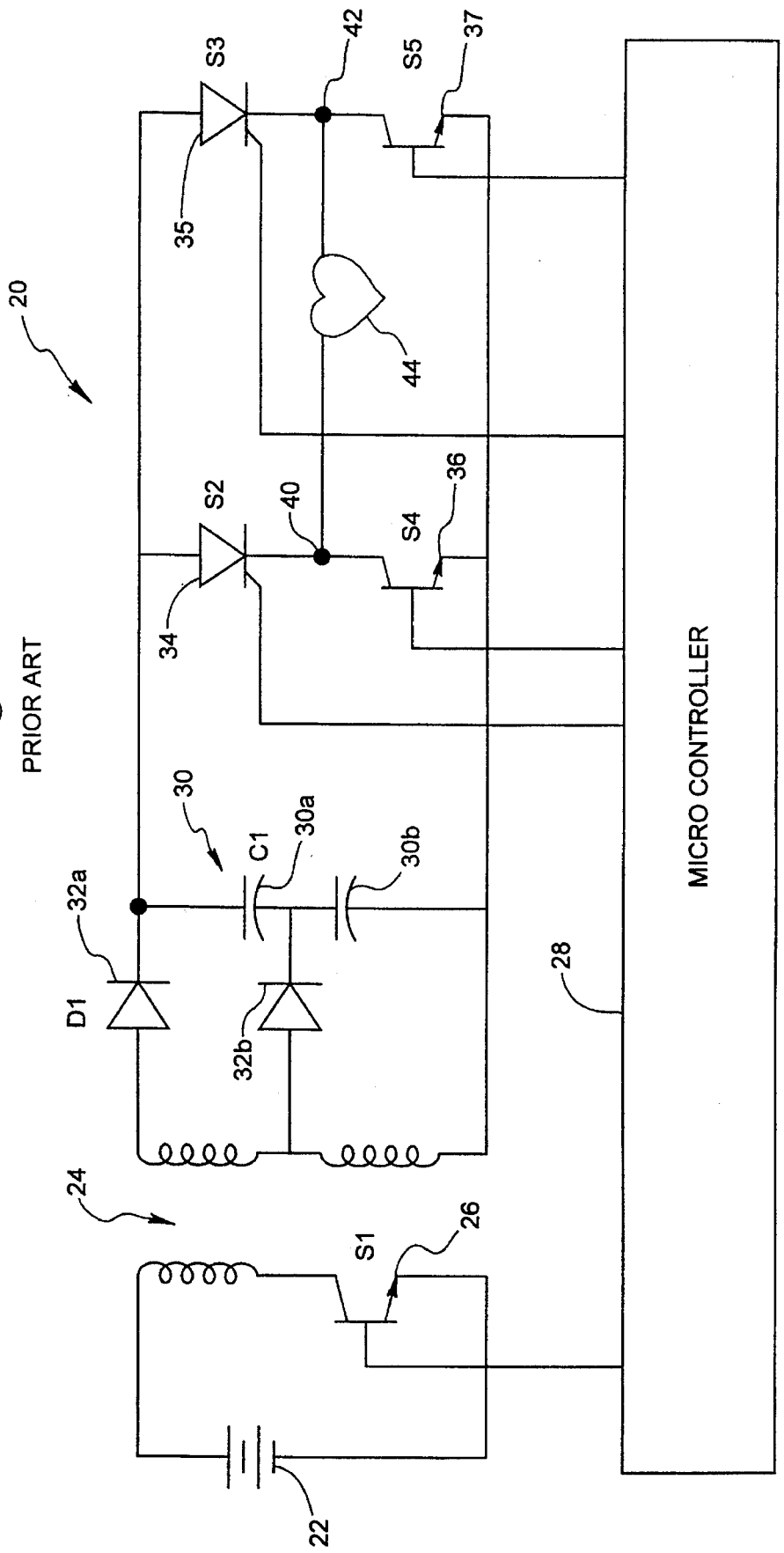
FIG. 2 is a schematic diagram of the circuitry in existing ICD systems that is used to produce the biphasic waveform as shown in FIG. 1.

FIG. 2 shows a schematic diagram of the circuitry 20 that is used in existing implantable cardioverter defibrillator (ICD) systems to produce biphasic waveform 10 as shown in FIG. 1. Battery system 22 activates a primary winding on flyback split winding transformer 24 when switch 26 is activated by controller 28. Each of the split secondary windings of transformer 24 charges capacitor system 30, consisting of a pair of electrolytic capacitors 30a or 30b, through diode 32a or 32b, respectively. Switches 34, 35, 36 and 37 are connected in a conventional H-bridge switch arrangement as shown to electrodes 40 and 42 to deliver biphasic waveform 10 to the heart 44. During delivery of first phase 12, switches 34 and 37 are closed and switches 35 and 36 are open. At the transition point at the end of first phase 12 and the beginning of second phase 14, controller 28 opens switches 34 and 37 and closes switches 35 and 36 to reverse the polarity and current flow of the countershock delivered through electrodes 40 and 42, thereby producing biphasic waveform 10. An example of circuitry 20 is shown and described in further detail in U.S. Pat. No. 4,998,531.

As indicated in the background section, the transition point between the end of first phase 12 and the beginning of second phase 14 is determined according to one of two techniques, variable duration tilt-based control or fixed duration time-based control. In the case of a variable duration tilt-based operation, controller 28 dynamically measures the rate of decay of the capacitive-discharge from capacitors 30a and 30b until the output voltage reaches some predetermined tilt value defined for the transition point, after which controller 28 causes circuitry 20 to change from first phase 12 to second phase 14. In the case of a fixed duration time-based operation, controller 28 measure the time elapsed since the start of first phase 12 and when the elapsed time reaches some predetermined time value defined for the transition point, controller 28 causes circuitry 20 to change from first phase 12 to second phase 14. It will be apparent that the duration of both the first and second phases of a biphasic countershock delivered using a tilt-based control technique will be variable and will depend upon the actual charging and discharging characteristic for capacitors 30a and 30b at the time of the discharge, as well as the actual inter-electrode resistance observed between electrodes 40 and 42 during the discharge. In contrast, the duration of the first and second phases of a biphasic countershock delivered using a time-based control technique will be fixed and will be independent of any of the factors which affect delivered of a biphasic waveform using the tilt-based control technique.

It should also be understood that by charging and discharging capacitors 30a and 30b in series, the effectiveness capacitance of capacitor system 30 is the series combination of the individual capacitance values of capacitors 30a and 30b, i.e., one-half of each of the individual capacitance values, while the discharge voltage can be twice the maximum charging voltage of the individuals capacitors 30a or 30b. In this way, electrolytic capacitors which have a relatively higher energy density, but which have a maximum charging voltage of only about 375 volts, can be used in an ICD system that need to generate defibrillation countershocks having discharge voltages of at least 500 volts. It will be further understood that electrodes 40 and 42 are shown by way of example and that cardiac electrodes of any conventional type may be used with the present invention, that more than two electrodes may be utilized for delivering a countershock waveform and that different electrode sets may even be used to deliver the different phases of the biphasic countershock waveform.

Defibrillation at the Cellular and Tissue Level

Before describing the model for biphasic waveforms which is proposed and utilized by the present invention, it is important to review the present understanding of defibrillation at the cellular and tissue level. While defibrillation is presently understood fairly well at the cellular and tissue level for monophasic waveforms, as indicated by the numerous theories purporting to explain the efficacy of biphasic waveforms, there is no general understanding at the cellular and tissue level for biphasic waveforms.

Monophasic Waveform at the Cellular and Tissue Level—There is now strong evidence, from optical recordings, that the monophasic shock defibrillates by resynchronizing a large majority (i.e., at least 90%) of the myocardial cells. Dillon SM, "Synchronized Depolarization after Defibrillation Shocks: A Possible Component of the Defibrillation Process Demonstrated by Optical Recordings in Rabbit Heart", *Circulation* 1992;85:1865–1878. The requirement that a monophasic countershock resynchronize the large majority of myocardial cells is apparently due to the fact that a defibrillation strength shock will not only stimulate recovered cells (i.e. those in phase 4 or electrical diastole), but will also extend the activation potential of those already activated cells. This has been supported by non optical measurements showing that monophasic defibrillation shocks are indeed capable of extending the refractory period of activated cells in dogs, Sweeney RJ, Gill RM, Steinberg MI, et.al., "Ventricular Refractory Period Extension Caused by Defibrillation Shocks", *Circulation* 1990;82:965–972; and humans, Belz MK, Speery RE, Wood MA, Ellenbogen KA, Stambler BS, "Successful Defibrillation Prolongs Action Potential Durations in Humans", *PACE* 993;16:932 (Abstract).

These results have created two semantic problems. First, it is now clear that the "absolute refractory" period is not absolutely refractory. It merely requires defibrillation strength shocks for stimulation. The second problem lies with the use of the word "stimulation". Stimulation has been traditionally used (in the narrow sense) as referring to electrical initiation of a new activation potential by opening the voltage gated sodium channels. While it appears that the activation potential prolongation is indeed initiated by the reopening of the sodium channels, this is not characteristic of conventional pacing stimulation, for example. To minimize confusion, the present invention will use the term "countershock stimulation" in reference to cell stimulation in a defibrillation context.

The difference between convention pacing stimulation and countershock stimulation may help to partially explain the nature of the defibrillation process. For example, the chronaxie time for far-field stimulation (in the conventional pacing sense) is on the order of 1 ms. Frazier DW, Krassowska W et al., "Extracellular Field Required for Excitation in Three-Dimensional Anisotropic Canine Myocardium.", *Circulation Research* 1988;63:147–164. The chronaxie time for the monophasic defibrillation pulse, on the other hand, has been consistently found to be in a range of 2–4 ms. Wessale JL, Bourland JD, Tacker WA, et al, "Bipolar catheter defibrillation in dogs using trapezoidal waveforms of various tilts", *J Electrocardiology* 1980; 13 (4):359–366; Niebauer MJ, Babbs CF, Geddes LA, et al, "Efficacy and safety of defibrillation with rectangular waves of 2 to 20 milliseconds duration", *Crit. Care Medicine* 1983; 11 #2:95–98. A critical part of the defibrillation synchronization may be the countershock stimulation occurring in the refractory period. The increased difficulty of countershock stimulation in the so-called absolute refractory period may explain why the chronaxie time is increased from around 1 ms for pacing stimulation to around 3 ms for countershock stimulation.

Biphasic Waveform at the Cellular and Tissue Level—The exact mechanisms of biphasic defibrillation are not generally understood. Several qualitative findings exist, however, that, when properly interpreted, may give guidance towards an understanding of its mechanisms. These are that the biphasic waveform: (1) is an inferior stimulator compared to the monophasic waveform; (2) has less of a refractory period prolongation; and (3) has less post shock arrhythmias.

Biphasic is an Inferior Stimulator—Animal studies have compared the stimulation biphasic waveforms to that of monophasic waveforms and found that a biphasic pacing waveform required increased stimulus currents in relative refractory tissue, Wharton JM, Richard VJ, Murry CE, et.al. "Electrophysiological Effects In Vivo of Monophasic and Biphasic Stimuli in Normal and Infarcted Dogs", *PACE* 1990;13:1158–1172; and that a biphasic defibrillation waveform was less effective in countershock stimulating partially refractory myocardium. Daubert JP, Frazier DW, Wolf PD, et.al. "Response of Relatively Refractory Canine Myocardium to Monophasic and Biphasic Shocks", *Circulation* 1991;84:2522–2538.

Biphasic has Smaller Refractory Period—Another animal study measured the activation potential prolongation from a shock delivered at a 50% repolarization point. A symmetric biphasic waveform was compared to monophasic waveforms. The biphasic waveform was able to generate a significantly smaller action potential prolongation for equal voltage shocks. Zhou X, Knisley SB, Wolf PD, et.al., "Prolongation of Repolarization Time by Electric Field Stimulation with Monophasic and Biphasic Shocks in Open Chest Dogs", *Circulation Research* 1991;68:1761–1767.

Biphasic has Fewer Post Shock Arrhythmias—It has been already mentioned that the biphasic waveform generates less post shock arrhythmias. It has also been shown that the conduction block is less severe for the biphasic wave versus the monophasic wave and, for equal strength shocks, persists for less time. Yabe S, Smith WM, Daubert JP, et.al., "Conduction Disturbances Caused by High Current Density Electric Fields", *Circulation Research* 1990 ;66:1190–1203.

New Model For Biphasic Waveforms

Even with all of this information assembled, there is still no clear explanation for why the biphasic waveform is more efficient that the monophasic waveform. Consequently, there is no clear guidance on how, or even if, improvements can be made to the generation and delivery of biphasic waveforms. The present invention offers a model for the biphasic waveforms that appears to explain why delivery of a biphasic waveform in accordance with the present invention having a variable duration first phase and a fixed duration second phase is more efficacious than the existing technique of delivering biphasic waveforms from a single capacitor system.

The gist of the model that is utilized by the present invention is that the second phase of the biphasic waveform (when optimally sized) serves to remove the excess charge remaining on the cell membrane from the first phase. It is hypothesized that the excess charge remaining on cells after the countershock stimulation may end up creating a new arrhythmia some time after the countershock stimulation. Consequently, for a monophasic shock to be successful, it must not only capture enough cells to halt fibrillation, but it must also capture enough cells so that no post shock arrhythmias as a result of the excess charge remaining on the cell membrane will occur. In other words, by having the second phase of a biphasic countershock return the cell membrane potentials to their pre-shock potential, there are fewer post shock arrhythmias, and, because there are fewer post shock arrhythmias, fewer cells need to be synchronized by the first phase. In addition, the protective refractory period extension requirement may be reduced. It is theorized that these two factors may explain the reduced amplitude requirements for the first phase.

The circuit model of the cell that is implicit in this discussion is essentially the standard capacitive membrane coupled to resistive paths giving a membrane time constant. Fozzard HA, "Membrane Capacity of the Cardiac Purkinje Fiber", *J Physiol (Great Britain)* 1966;182:255–267. In this model, $V_e$ represents the voltage across the defibrillation electrodes and $V_m$ represents the voltage across the membrane. The exact values of the resistances and capacitance are not important, the salient feature is the resulting membrane time constant which will be called $\tau_m$.

Referring again to FIG. 1, the voltages are shown as a function of time which would be expected in such a model for a biphasic waveform delivered from an existing ICD system having a single capacitor system. Assuming an ICD capacitance of 150 µF and an electrode resistance of 50 Ω, the electrode voltages will be as shown for a biphasic wave, with each phase having a fixed duration of 3.5 ms. For ease of notation, the remaining discussion will refer to the durations of both phases of a fixed duration time-based biphasic waveform in a shorthand form as "3.5/3.5", indicating that the first phase is 3.5 ms and the second phase is 3.5 ms. Similarly, the durations of both phases of a variable duration tilt-based waveform will be referred to as "65%/32.5%", indicating a first phase duration having a 65% tilt and a second phase duration having a tilt that is one-half of the tilt of the first phase. The capacitor voltages 12 and 14 for the first and second phases of the waveform 10 are shown beginning at a normalized value of 1.00 volts at 18. The membrane voltages 16 are calculated with the use of a representative time constant of the non-Purkinje ventricular cell membrane of approximately 3 ms. Weidmann S, "Electrical Constants of Trabecular Muscle from Mammalian Heart", *J Physiol (Great Britain)* 1970; 210: 1041–1054.

The exact transmembrane potential of an individual cell as shown in FIG. 1 is not relevant for this analysis. What is important is the perturbation, by the first phase 12 of the defibrillation countershock, of the membrane voltage 16 from its existing value. The model of the biphasic waveform utilized by the present invention suggests that the cancellation of this perturbation, i.e. the "burping" of the membrane charge, appears to be the critical function of the second phase. As can be seen from FIG. 1, at the end of the second phase, the transmembrane potential has been left, in this case, with a negative perturbation potential 19 as a result of the delivery of the biphasic waveform, instead of the desired zero perturbation potential which is the goal of the theory of the present invention.

The membrane voltage $V_m$ is calculated as a fraction of the maximum potential attainable for an infinitely long rectangular pulse at the electrodes. The absolute value of the potential (in volts) is not critical as the return to zero is the sole goal of the biphasic waveform in accordance with the theory of the present invention. During the defibrillation shock the electric field will charge areas of the cell membrane positively, some negatively, and some not at all. Knisley SB, Blitchington TF, Hill BC, "Optical Measurement of Transmembrane Potential Changes During Electric Field Stimulation of Ventricular Cells", *Circulation Research* 1993;72:255–270. Also, depending upon the location of the cells vis-à-vis the electrodes, the actual membrane voltage will vary significantly. Using a normalized value (i.e. a fraction) for $V_m$ allows the model to concentrate on the simple goal of returning the membrane voltage to a zero perturbation.

Figure 3:
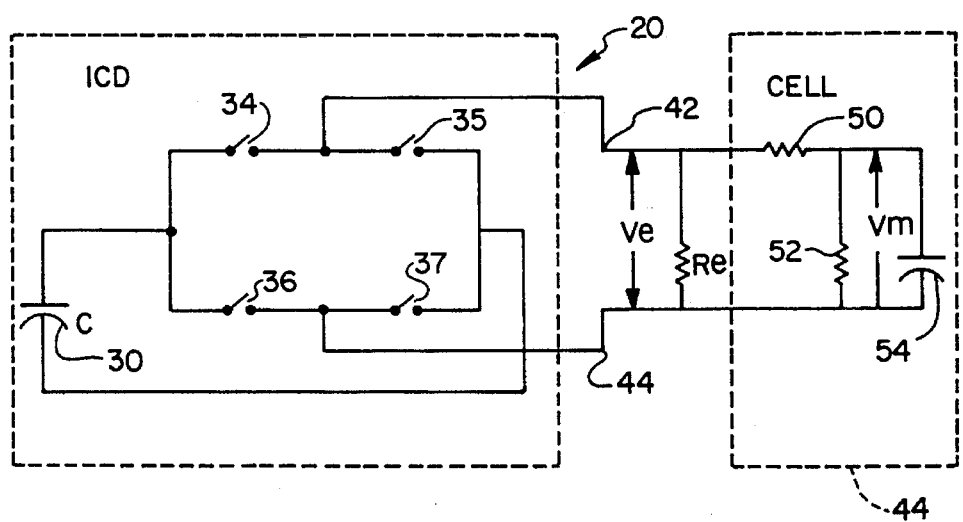
FIG. 3 is a simplified schematic diagram of the ICD system shown in FIG. 2 and including an electrical cell model of the heart.
Figure 4:
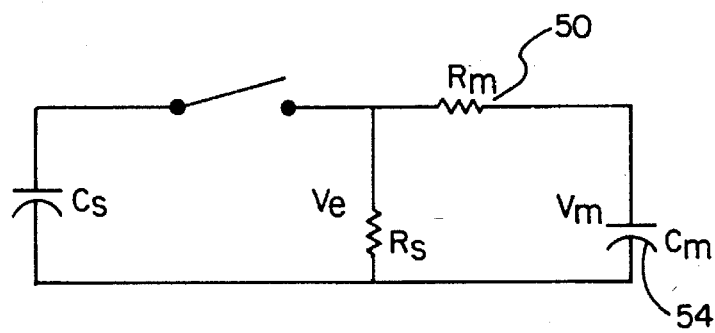
FIG. 4 is a further simplified schematic diagram of the ICD system shown in FIG. 3.

A quantitative model for the present invention can be determined with reference to FIGS. 3 and 4 which are schematic diagrams of an existing ICD system, of the type shown in FIG. 2, but coupled to a schematic lumped model of the electrical characteristics of the myocardial cells. FIG. 3 shows a circuit model of ICD system 20 and a representative myocyte cell of heart 44. ICD system 20 includes a main energy storage capacitor system 30 having an effective capacitance "C." To the right is the conventional H-bridge circuit with switch 34, 35, 36 and 37 for inverting the current flow for the two phases of the biphasic waveform. "$R_e$" is the inter-electrode resistance as shown at 46. Further to the right is a combination of a series resistor 50, a shunt resistor 52, and a membrane capacitance 54 for the analysis of the response of a representative cell to the defibrillation currents. The exact values of the resistances and capacitance are not important. The relative contribution to the time constant of the series resistances and the shunt resistances (from the so called leaky-capacitor model) is also not important. The salient feature is the resulting membrane time constant which will be called $\Omega_m$. $V_e$ represents the voltage across the defibrillation electrodes 42 and 44 and $V_m$ represents the voltage across the membrane 44.

Consider the simplified schematic of FIG. 4 for analyzing the first phase of a biphasic countershock, or all of a monophasic shock. In FIG. 4, the H-bridge circuit of FIG. 3 is temporarily ignored and the resistance 52 in parallel with the membrane capacitance 54 is eliminated in favor of simplicity. This parallel (leaky membrane) resistance 52 may be ignored if $R_m$ is taken as the Thevenin equivalent of the two resistors 50 and 52. Thus, $R_m$ and $C_m$ are the membrane series resistance and capacitance respectively. As before, the node $V_e$ represents the voltage between the electrodes, while $V_m$ denotes the voltage across the cell membrane. Nodal analysis provides an equation for the solution of $V_m$:

$$C_m[(dV_m/dt)] + [(V_m - V_e)/R_m] = 0. \tag{1}$$

Rearranging equation 1 to solve for $V_e$, we have $$V_e = V_m + (R_m C_m)(dV_m/dt) \tag{2}$$

The discharge of a single capacitor in such a circuit is well-known, is modeled by $$V_e = e^{(-t/R_s C_s)},$$

and so may be placed into equation 2 to give:

$$\tau_m (dV_m/dt) + V_m = e^{(-t/\tau_S)}, \tag{3}$$

where $\tau_m = R_s C_s$ represents the time constant of the myocardial cell in the circuit model, and is $\Omega_s = R_s C_s$ represents the time constant of the defibrillator shock in the circuit model. This differential equation models the effects of a monophasic, time-truncated, capacitor-discharge defibrillator on the myocardium.

Equation 3 is a first-order linear differential equation, and may be written as $$\frac{dV_m}{dt} + \left(\frac{1}{\tau_m}\right) V_m = \left(\frac{1}{\tau_m}\right) e^{(-t/\tau_s)}. \tag{4}$$

In the form of equation 4, the general solution is $$V_m = e^{-t/\tau_m} \left( \int \left( e^{t/\tau_m} \left(\frac{1}{\tau_m}\right) e^{-t/\tau_s} \right) dt + c \right). \tag{5}$$

where c is an integration constant. Integrating equation 5 and simplifying the resultant expression, we have for the membrane voltage at the end of the first phase:

$$V_{m1}(t) = ce^{-t/\tau_m} + [\tau_s/(\tau_s - \tau_m)] e^{-t/\tau_S}. \tag{6}$$

To determine the constant of integration c, we assume the initial value for $V_m$ to be $V_m(0) = 0$. Applying the initial condition to equation 6, we have $$c = -[\tau_s/(\tau_s - \tau_m)]$$

Therefore, the solution to our initial-value problem for phase 1 is $$V_{m1}(t) = [\tau_s/(\tau_s - \tau_m)](e^{-t/\tau_S} - e^{-t/\tau_m}). \tag{7}$$

A biphasic waveform reverses the flow of current through the myocardium during the second phase. The simplified model of FIG. 4 may again be used by merely reversing the flow of current in the circuit model by changing the sign on the shock current. We thus derive an almost identical differential equation to equation 3 above. The difference is the sign on the right hand side:

$$\tau_m(dV_m/dt) + V_m = -e^{(-t/\tau S)}. \tag{8}$$

At the beginning of phase 1, we assumed a normalized value of 1 for the charge found on the capacitor at the time the defibrillation shock was initiated, so that equation 3 may be more explicitly written as $$\tau_m(dV_m/dt) + V_m = 1 \cdot e^{-t/\tau S}.$$

At the beginning of phase 2, the capacitor has discharged for a period of time equal to the length of phase 1, and we shall denote this time period as $d_1$ (the duration of phase 1). The normalized capacitor charge at the start of phase 2 is therefore $e^{31\ d1/\tau d} < 1$, and so equation 8 may be written more explicitly as $$\tau_m(dV_m/dt) + V_m = -e^{-d1/\tau S} \cdot e^{-t/\tau S}. \tag{9}$$

Equation 9 is again a first-order linear differential equation, and we write this equation in the form below to apply standard methods for determining its solution:

$$\frac{dV_m}{dt} + \left(\frac{1}{\tau_m}\right)V_m = -\left(\frac{1}{\tau_m}\right) \cdot e^{-d_1/\tau_s} \cdot e^{-t/\tau_s} \quad (10)$$

In the form of equation 10, the general solution is $$V_{m2}(t) = ce^{-t/\tau m} - [\tau_s/(\tau_s - \tau_m)] \cdot e^{-d_1/\tau S} \cdot e^{-t/\tau S} \quad (11)$$

To determine the constant of integration c, we note that at the end of phase 1 the (initial) value for $V_{m2}$ is $$V_{m2}(0) = V_{m1}(d_1) = [\tau_s/(\tau_s - \tau_m)](e^{-d_1/\tau S} - e^{-d_1/\tau m}).$$

Applying the initial condition to equation 11, we have $$c = [\tau_s/(\tau_s - \tau_m)]K_m$$

where $$K_m = 2e^{-d_1/\tau S} - e^{-d_1/\tau m}.$$

Therefore, the solution to the initial-value problem for phase 2 is $$V_{m2}(t) = -[\tau_s/(\tau_s - \tau_m)](K_s e^{-t/\tau S} - K_m e^{-t/\tau m}) \quad (12)$$

$$K_s = e^{-d_1/\tau S}.$$

which may be rewritten as:

$$V_{m2} = [\tau_s/(\tau_s - \tau_m)][(2e^{-d_1/\tau S} - e^{-d_1/\tau m})e^{-d_2/\tau m} - e^{-d_1/\tau s}e^{-d_2/\tau S}] \quad (13)$$

The requirement defining an optimal pulse duration for phase 2 is that the phase 2 pulse leave as little residual membrane potential remaining on a non-depolarized cell as possible. Equation 12 provides a means to calculate the residual membrane potential at the end of the second phase for those cells that did not depolarize. To determine the optimal phase 2 pulse duration, we set equation 12 equal to zero and solve for t. This optimal pulse duration for phase 2, then, is $d_2$. To begin, we have $$0 = -[\tau_s/(\tau_s - \tau_m)](K_s e^{-t/\tau S} - K_m e^{-t/\tau m}).$$

Because $(\tau_s/(\tau_s - \tau_m))$ cannot be zero, we solve for t using the equation $$0 = K_m e^{-t/\tau m} - K_s e^{-t/\tau S}.$$

Arranging the exponential functions onto the left hand side, we get $$(e^{-t/\tau S}/e^{-t/\tau m}) = K_m/K_s. \quad (14)$$

Taking the logarithm of each side, solving for t, and rearranging terms, we get $$t = \left(\frac{\tau_s \tau_m}{\tau_s - \tau_m}\right) \cdot \ln\left(\frac{K_m}{K_s}\right) \quad (15)$$

$$d_2 = \left[\frac{\tau_s \tau_m}{\tau_s - \tau_m}\right] \cdot \ln\left\{2 - \left[\frac{e^{-d_1/\tau m}}{e^{-d_1/\tau s}}\right]\right\}. \quad (16)$$

For typical values of a 140 μF capacitor and a 50 Ω electrode resistance the time constant ($\tau_s$) will be 7 ms. Assume that $\tau_m$ is the membrane time constant. The durations of the two phases will be referred to as $d_1$ and $d_2$ respectively. The membrane potential at the end of phase one will be given by Equation 7 as $$V_{m1} = (\tau_s/(\tau_s - \tau_m))[(e^{-d_1/\tau S} - e^{-d_1/\tau m})]$$

The subtraction of the two exponentials represents the attempt by the discharge capacitor of the ICD (as represented by the positive term with time constant $\tau_s$) to charge the membrane while the membrane capacitance is resisting the charging with its electrical inertia (as represented by the negative term containing $\tau_m$).

The membrane voltage at the end of the second phase is given as the following equation rearranged from Equation 12:

$$V_{m2} = (\tau_s/(\tau_s - \tau_m))[(2e^{-d_1/\tau S} - e^{-d_1/\tau m})e^{-d_2/\tau m} - e^{-d_1/\tau S}e^{-d_2/\tau}] \quad (17)$$

This intimidating equation is necessary to reflect the interaction between the two phase durations and two the time constants.

The fundamental hypothesis of the model of the present invention is that a low residual membrane voltage lowers the electrical requirements of the first phase. This presents an interesting tautological question. How can the second phase affect the first phase when the first phase precedes it?. More anthropomorphically, the first phase doesn't even know that the second phase is coming. The answer is as follows: The lower residual membrane voltage (as a result of the second phase of the shock) reduces the necessary current (of phase one) that would otherwise be required to extinguish the additional local arrhythmias caused by the higher residual membrane voltage.

The electrical content of the first phase could be represented in many fashions. To correct for varied durations, the "effective" current model is used as set forth in the previously identified co-pending application entitled IMPLANTABLE CARDIOVERTER DEFIBRILLATOR HAVING A SMALLER DISPLACEMENT VOLUME. The effective current is simply the average current divided by the "duration correction". The effective current is also equal to the rheobase current for shocks exactly at the threshold level. The function of the duration correction is to normalize the average current for the higher requirements of narrower pulses which is given by the strength duration curve.

The duration correction is:

$$1 + (d_c/d) \quad (18)$$

and thus the effective current is given by:

$$I_{eff} = I_{ave}/[1 + (d_c/d)] \quad (19)$$

The model of the present invention predicts that the required effective current has a minimum value which will be referred to as $I_o$ for a perfectly shaped biphasic wave leaving a zero residual membrane potential. The model then further predicts that the increase in required effective current from this $I_o$ value is proportional to the excess membrane potential squared. In other words:

$$I_{eff} = I_o + kV_m^2 \quad (20)$$

Application of the New Model

To begin with, the new model will be applied to the known characteristics and experimental results of biphasic waveforms to see whether the model accurately predicts these.

Model Agreement with Reduction in Post Shock Arrhythmias—This new model does not purport to explain all of the findings of reduced post shock arrhythmias. A fundamental tenet of the model, however, is that the increased efficacy of the biphasic waveform is due to reduction in these arrhythmias. Thus, it is axiomatic that this finding is congruent with the model as it is on of the primary hypotheses of the model.

Figure 5:
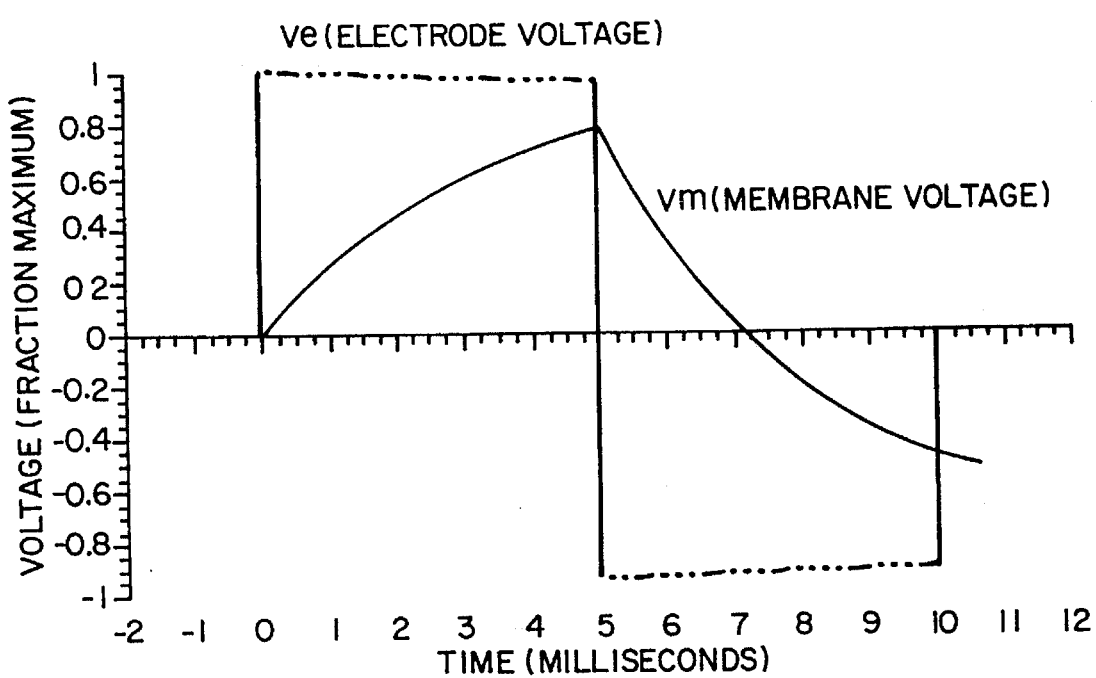
FIG. 5 is a graph of the electrode and membrane voltages for a 5/5 ms biphasic waveform from a 2000 μF capacitor and 50 Ω electrode resistance that approximates a symmetric biphasic waveform.

Explanation of the Minimal Benefit of the Symmetrical Waveform—As observed earlier, biphasic waveforms with symmetrical phases have been shown to offer minimal or no benefit—certainly for defibrillation thresholds in terms of energy (as opposed to a square-wave voltage). An analysis of FIG. 5 explains why this result might be seen in the animal model and in this quantitative model. To approximate a symmetrical biphasic waveform a large capacitor (2000 μF) and a 50 Ω electrode is assumed. A 5/5 ms biphasic waveform is then produced. Note that the two phases are fairly symmetric. The cell membrane voltage is noted to rise to about 0.75 during the first phase and then fall rapidly during the second phase. Because the current flow is reversed between the phases, the cell membrane is discharged more rapidly during this second phase than it was charged during the first phase. Therefore the cell voltage is "pulled through" zero during the second phase and is left at a high negative potential of about 0.5. This potential is ⅔ as large in magnitude as that which was found at the end of the first phase.

As can be seen, the second phase did not serve to remove residual cell voltage—but rather served primarily to change its polarity. The present model suggests that there is no advantage in having a mere polarity change in the residual cell voltage 19. Thus the symmetric biphasic should have only a minimal advantage over the monophasic waveform for defibrillation thresholds.

Model Explanation for Benefit of a Shorter Second Phase—As previously indicated, several earlier studies have shown that it is important that, at least in a single capacitor biphasic waveform, that the duration of the second phase be less than or equal to the duration of the first phase. The equations given earlier can be solved to show the relationships between the two different phase durations. It can be directly shown, for reasonable electrode resistances and presently used capacitance values in a single capacitor system, that the second duration should be always smaller than the first—for the lowest threshold.

This finding can also be derived directly from the model from a review of the membrane and electrode voltages in FIG. 1. Again the basic principal is that the discharge rate in the second phase is greater than the charge rate during the first phase. Therefore if the first phase was equal in amplitude and duration to the second phase the second phase would still leave a large reverse voltage membrane potential 19. This is true even for the unequal phase voltages seen with practical capacitor sizes.

Consider for example the 150 μF capacitor used for the example in FIG. 1. Even though the capacitor is discharging at a sufficient rate so that the electrode voltage in the second phase is significantly lower than that of the first phase, the membrane discharge rate is still significantly greater in phase two. In a fixed-duration system, the membrane capacitance was charged for 3.5 ms during the first phase. A close inspection in FIG. 1 shows that the membrane capacitance would be fully discharged in a little over 2 ms of the second phase. If the second phase was equal in duration to the first phase (i.e. total duration =7 ms) then the membrane potential would be seen to be negative and thus non optimal. However, that negative potential would still be closer to zero than that which would have occurred with no second phase (i.e. with a 3.5 ms monophasic waveform). For this reason single capacitor waveforms in which both phases are equal still offer benefits over the monophasic waveforms. Nevertheless, they are not the optimal biphasic waveform for presently used capacitor values. As taught by the present invention, however, this is not true for smaller, and possibly more optimal, values of capacitances, as well as for disparate dual capacitor systems.

Model Explanation for the Reduced Transthoracic Advantage—Transthoracic defibrillation may produce a more symmetrical distribution of current and potential gradients in the heart than is found with epicardial defibrillation. This would imply that the ratio of minimum to maximum fields is much lower with transthoracic defibrillation that it is with epicardial defibrillation. Therefore, with a shock of sufficient strength to synchronize the overwhelming majority of the heart, there is a much lower likelihood of a substantial mass of cells being partially stimulated and with pro-arrhythmic residual charges. Thus, the "burping" action of the second phase would act on a much smaller population of cells for the transthoracic case than it would for the epicardial defibrillation case. This would reduce the benefit of the second phase and hence of the biphasic wave itself.

Deleterious Effects of the Residual Charge—The residual charge may interfere with defibrillation at two extremes. In the first case the excessive field will leave a charge on the membrane which is intrinsically harmful and proarrhythmic. In the second case a borderline stimulation field will fail to assertively capture and hence synchronize the cell. For both of these cases an implicit hypothesis of the model of this invention is that (at least some) of the deleterious effects of the shock are prevented or minimized by immediately removing the residual charge left by the shock.

Direct experimental data supporting this hypothesis is limited. It is accepted that repolarizing current pulses will reduce the incidence of early after depolarizations. January CT, Shorofsky S., "Early After depolarizations: Newer Insights into Cellular Mechanisms", *J Cardiovascular Electrophysiology* 1990;1:161–169. Indirect evidence in favor of the second effect (borderline stimulation) was found in studies that showed that the first reactivation, following an unsuccessful monophasic shock, is in the area that had received the smallest electrical field. Shibata N, Chen PS, Dixon EG, et. al., "Epicardial Activation After Unsuccessful Defibrillation Shocks in Dogs", *American J Physiology* 1988;255:H902-H909; Chen PS, Shibata N, Dixon EG. "Activation During Ventricular Defibrillation in Open-Chest Dogs", *J Clinical Investigation* 1986;77:810–823. Despite these results, the authors of these two studies concluded, "These findings suggested that the shock extinguished all of the activation fronts present during fibrillation, but, after a latency period, the shock itself gave rise to new activation fronts that caused fibrillation to be reinitiated." This conclusion is inapposite to the model of the present invention which concludes that it is the excess charge on the cell membranes, and not the shock itself, that would give rise to new activation fronts that would cause post shock arrhythmias.

Effects of Borderline Fields—As previously indicated, one of the possible consequences of the model of the present invention is an explanation of the borderline field phenomenon. Using the Hodgkin-Huxley model of invitro cell propagation that, when the local response has almost reached propagating size, it becomes unstable and varies from shock to shock, computer estimates of stimulation strength-duration curves have shown that ". . . a highly unstable subthreshold propagating wave is initiated in principle by a just threshold stimulus." Cooley JW, Dodge FA., "Digital Computer Solutions for Excitation and Propagation of the Nerve Impulse", *Biophysical Journal* 1966;6:583–599. Four different cellular models have also been studied with borderline strength stimulation, and all four models showed similar activation delays possible of 20, 12, ">20," and 8 ms respectively. Krassowska W, Cabo C, Knisley SB, et.al., "Propagation vs. Delayed Activation During Field Stimulation of Cardiac Muscle", *PACE* 1992;15:197–210. Latencies and other graded responses also have been experimentally observed in mammalian cardiac tissue. Kao CY, Hoffman BF, "Graded and Decremental Response in Heart Muscle Fiber",*American J Physiology* 1958;194 (1):187–196.

The above results suggest an intriguing possibility extending from the present model. When the shock is delivered to the heart, at threshold, there are regions of the heart that will receive an insufficient field for countershock stimulation. In the transition zone between these non-stimulated cells and the stimulated cells, there will be cells that will receive a borderline stimulation of the type which has been analyzed by this model. These borderline stimulated cells would then be activated with a significant delay or an unstable response. This could be sufficient to destroy the synchronization desired from the defibrillation shock. The second phase of the defibrillation shock, by removing that residual charge, may be able to arrest the delayed and unstable responses. This would then eliminate this source of de-synchronization.

Application of the New Model to Existing ICD Systems

As previously described, presently available ICD systems offer either the option of programmable tilts for both phases of the biphasic waveform, or the option of programmable durations for both phases of the biphasic waveform. According to the present model, the optimal durations for each phase of a biphasic waveform will be a function of 4 variables: the electrode resistance, the ICD capacitance, the chronaxie time, and the membrane time constant. The calculated values are fairly insensitive to changes in the chronaxie time and membrane time constant. The primary sensitivity is to the electrode resistance and ICD capacitance.

The ICD capacitance in present devices ranges from 85–180 µF. The electrode resistance varies from 25 Ω to 100 Ω depending upon the electrode system. In addition, the electrode impedance can vary over a 2:1 ratio from the time of implant to a 1 year follow-up. Schwartzman D, Jadonath R, Estapo J, et.al., "Ser. Patch—Patch Impedance Values in an Epicardial Defibrillation System", *PACE* 1993;16:916 (Abstract).

Optimal phase durations for single capacitor systems—Calculations are simplified by the fact that the value of the electrode resistance and ICD capacitance are combined in the simple electrical time constant of $\tau_s=RC$. As taught by the previously identified co-pending application entitled IMPLANTABLE CARDIOVERTER DEFIBRILLATOR HAVING A SMALLER DISPLACEMENT VOLUME, the first phase duration is given by that of the optimal monophasic pulse.

$$d_1 = 0.58\tau_s + 0.58 d_c \quad (21)$$

where $\tau_s=RC$ is the shock time constant and $d_c$ is the chronaxie duration. This formula codifies the necessary compromise between the electronics (having a sufficient duration to discharge the capacitor) and the heart (having a duration near the chronaxie time).

The equation giving the residual membrane voltage, for the end of phase 2, may be solved for the duration which restores the potential to a zero voltage (actually a zero departure from initial). The optimal value of the second phase duration is given by Equation 16:

$$d_2(\text{opt}) = [(\tau_s \tau_m)/(\tau_s - \tau_m)] \ln[2 - (e^{-d_1/\tau_m}/e^{d_1/\tau_s})] \quad (22)$$

Figure 6:
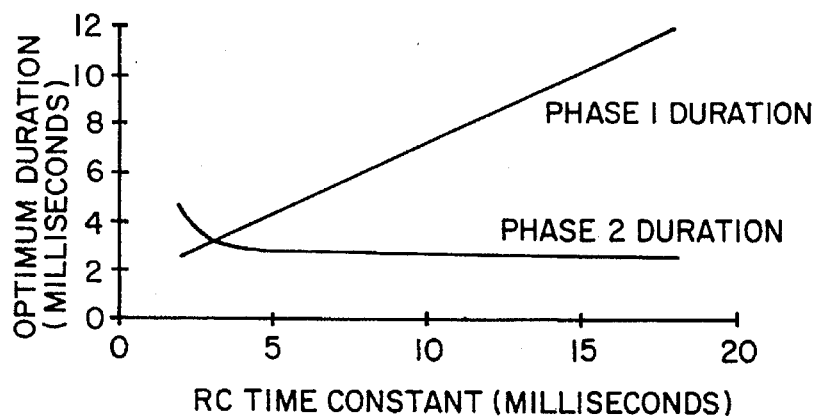
FIG. 6 is a graph of the optimum duration of the first and second phases of a single capacitor system biphasic waveform as a function of the RC time constant as derived by the biphasic model of the present invention.

The optimal durations for a single capacitor system are shown in FIG. 6. A chronaxie duration of 2.4 ms is assumed for phase one which is given by the top curve. The lower curve is the optimal phase two duration which is given by the $d_2$ equation above. Note that the phase one duration increases linearly with the time constant. Note that the phase two duration decreases initially and is essentially constant for increasing RC time constants. The phase 2 duration of 2.5 ms appears to be a reasonably accurate value regardless of the RC time constant (at least for present values of R and C).

At first it may seem counter-intuitive that the optimum phase two duration is essentially constant regardless of the RC time constant—especially while the phase one durations are changing. However, for a large RC time constant, there will be an increasing voltage remaining on the capacitor for use in the second phase. Thus a second phase will have a large discharge capability. At the same time, for the optimal first phase duration, the cell membrane voltage will be increased. These two factors tend to work in balance. In other words, there is a greater membrane charge to be discharged, but there is a greater capacitor charge and hence a greater discharge capability to be applied to the membrane.

Conversely, for the case of a smaller RC time constant (in the range of 4–6 ms) the capacitor is more discharged at the end of the first phase. Thus there is less discharge capability in the second phase of the biphasic wave. However this is balanced out by the fact that the cell membrane had less time to charge up and thus there is less to discharge from the cell membrane itself. These intuitive arguments, and the quantitative results from the model run counter to some standard practice, which is to make the second phase duration proportional to that of the first phase.

Figure 7:
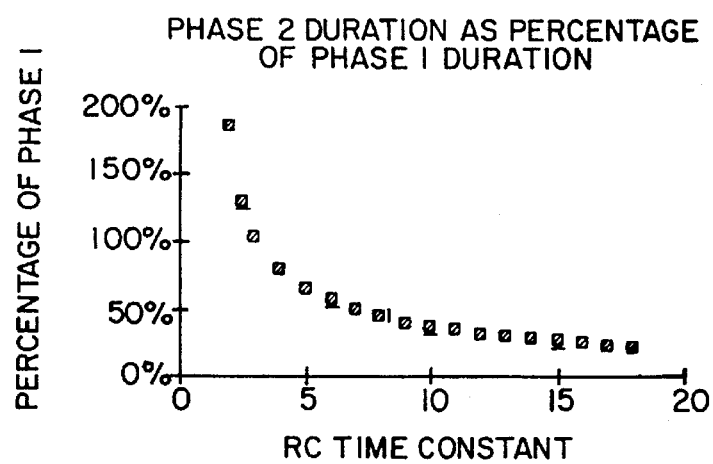
FIG. 7 is a graphs of the phase 2 duration as a percentage of the duration of phase 1 for optimal thresholds of a single capacitor system biphasic waveform according to the present model.

FIG. 7 shows how the optimal phase 2 duration for a single capacitor system varies as a percentage of that of phase one. It is seen that there is no constant relationship. The phase two duration, for an optimal biphasic wave, is 186% of the phase one duration for a $\tau_1=RC=2$ ms and falls steadily to only 21% of the phase one duration for $\tau_1=18$ ms.

Figure 8:
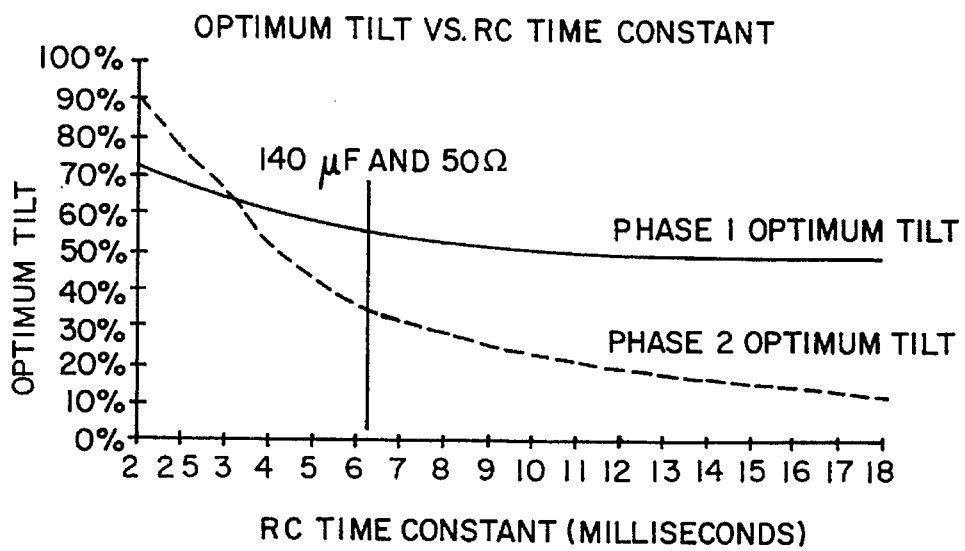
FIG. 8 is a graph of optimum tilts for phases 1 and 2 as a function of RC time constant for a single capacitor system according to present model.

Optimal tilts for each phase of a single capacitor system—Some existing ICD systems have durations specified as a "tilt". As can be seen in FIG. 8 the optimal tilt is reasonably constant for phase one regardless of the RC time constant. It varies between 50–65% for reasonable values. Thus its use is defensible. However, the phase two optimum tilt varies from 65% down to only 13% for a reasonable range of time constants. Thus the use of a tilt specification for the second phase of a biphasic waveform is probably not defensible. It is also probably not advisable to use a phase two duration which is defined as a percentage of the phase one duration (when that phase one duration itself is tilt defined).

Optimal capacitance for a single capacitor system—As taught by the previously identified co-pending application entitled IMPLANTABLE CARDIOVERTER DEFIBRILLATOR HAVING A SMALLER DISPLACEMENT VOLUME, the capacitance value of the capacitor system has a significant impact on defibrillation thresholds. The present biphasic model implicitly assumes that the optimum first phase of the biphasic waveform should be the same as the optimal monophasic waveform, because the function of the second phase is not to stimulate, but only to "burp" the residual charge. The monophasic modeling set forth in the above-identified application suggests that the optimum capacitance is given by choosing it such that:

$$\tau_s = RC = 0.8 d_c. \quad (23)$$

This gives a pulse width tuned to the chronaxie time and minimizes the stored energy requirements. The stored energy requirement determines the size of the ICD system and thus is critically important. For an assumed chronaxie time of 2.7 ms this suggests that:

$$\tau_s = RC = 2.16 ms$$

For a typical electrode impedance of 50 Ω one would have an optimal capacitance value of C =43.2 µF. The optimal pulse duration given by the earlier equation for phase one (or for the monophasic wave) would be 2.82 ms. The solution of the biphasic equations gives an optimal duration for phase two of about 6 ms. This suggests a phase two duration in excess of the phase one duration. While this is contrary to the reported results that phase 2 should be shorter than phase 1 for single capacitor systems, all of these results presumed capacitance values of greater than 140 µF. In addition, because the tilt for the optimum second phase would be over 95% (and not 100%), the single capacitor system, while nearly exhausted during the second phase, would still have some residual charge to meet the goal of discharging the membrane capacitance.

For the purposes of the present invention, the optimal durations of a biphasic waveform countershock generated by an implantable defibrillator system having an effective RC time constant $\tau_s$ of greater 2 ms is for the first phase to be of a variable duration depending upon the RC time constant $\tau_s$ and for the second phase to be of a fixed duration of between 2 to 4 ms that is independent of the RC time constant $\tau_s$. The RC time constants $\tau_s$ for all reported implantable defibrillators and reported ranges of interelectrodes resistances range from 1.3 ms to 39 ms based on effective capacitance values ranging from 85–300 µF and reported interelectrode resistances ranging from 16–130 Ω.

Alternatively, for RC time constants $\tau_s$ which are not above 2 ms, the optimal duration of the second phase of a biphasic waveform can be determined by reference to FIGS. 6 and 8 and Eqs. (12) and (16), in which case it will be seen that the optimal duration of the second phase of a biphasic waveform will be decreasing with increasing RC time constants $\tau_s$. In general, for most interelectrode resistances which are greater than about 25 Ω, the RC time constants $\tau_s$ will be greater than 2 ms for effective capacitance values of greater than 80 µF, in which case the duration of the second phase should be a fixed value of between 2 ms and 4 ms, and preferably about 2.5 ms. For interelectrode resistances that are less than about 75 Ω, the RC time constants $\tau_s$ will be less than 2 ms for effective capacitance values of less than 27 µF, in which case the duration for the second phase should be a variable value that decreases with an increase of the system time constant for the implantable defibrillator system. Between these two end condition areas of the curve as shown in FIG. 6, the relationship between the RC time constants $\tau_s$ and the optimum duration of the second phase of the biphasic countershock is best defined by Eq. (22). If Eq. (22) is used, solutions for the equation for the optimal second duration may be precalculated for a range of values for $d_1$, $\tau_s$, and $\tau_m$ and stored in a memory in the implantable defibrillator. The microprocessor that controls the setting of duration timer 94 for the second duration can then selectively choose among the stored solutions based on determined values for at least $d_1$ and $\tau_s$.

Figure 9:
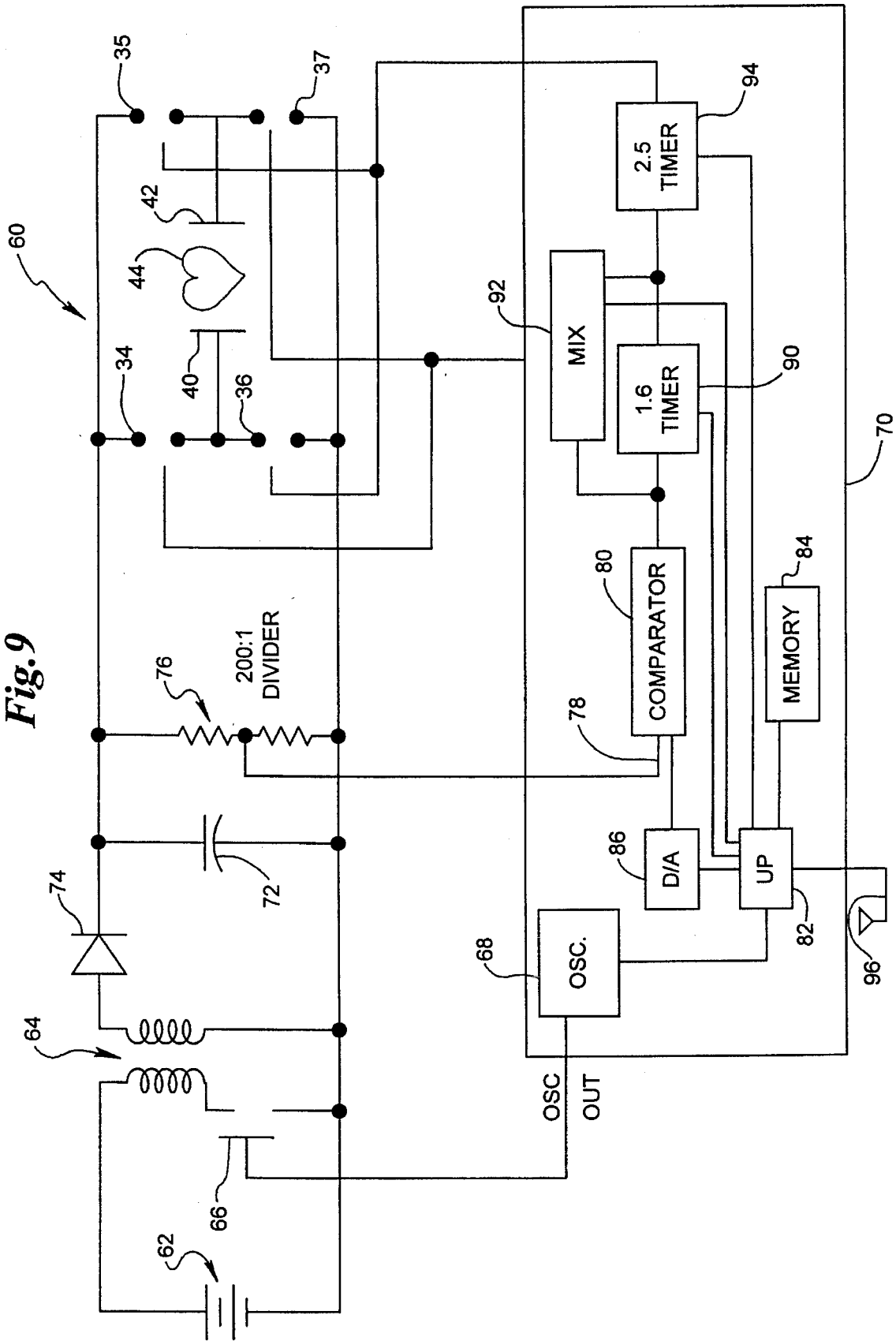
FIG. 9 is a circuit diagram of a preferred embodiment of an improved discharge control system in accordance with the present invention.
Figure 10:
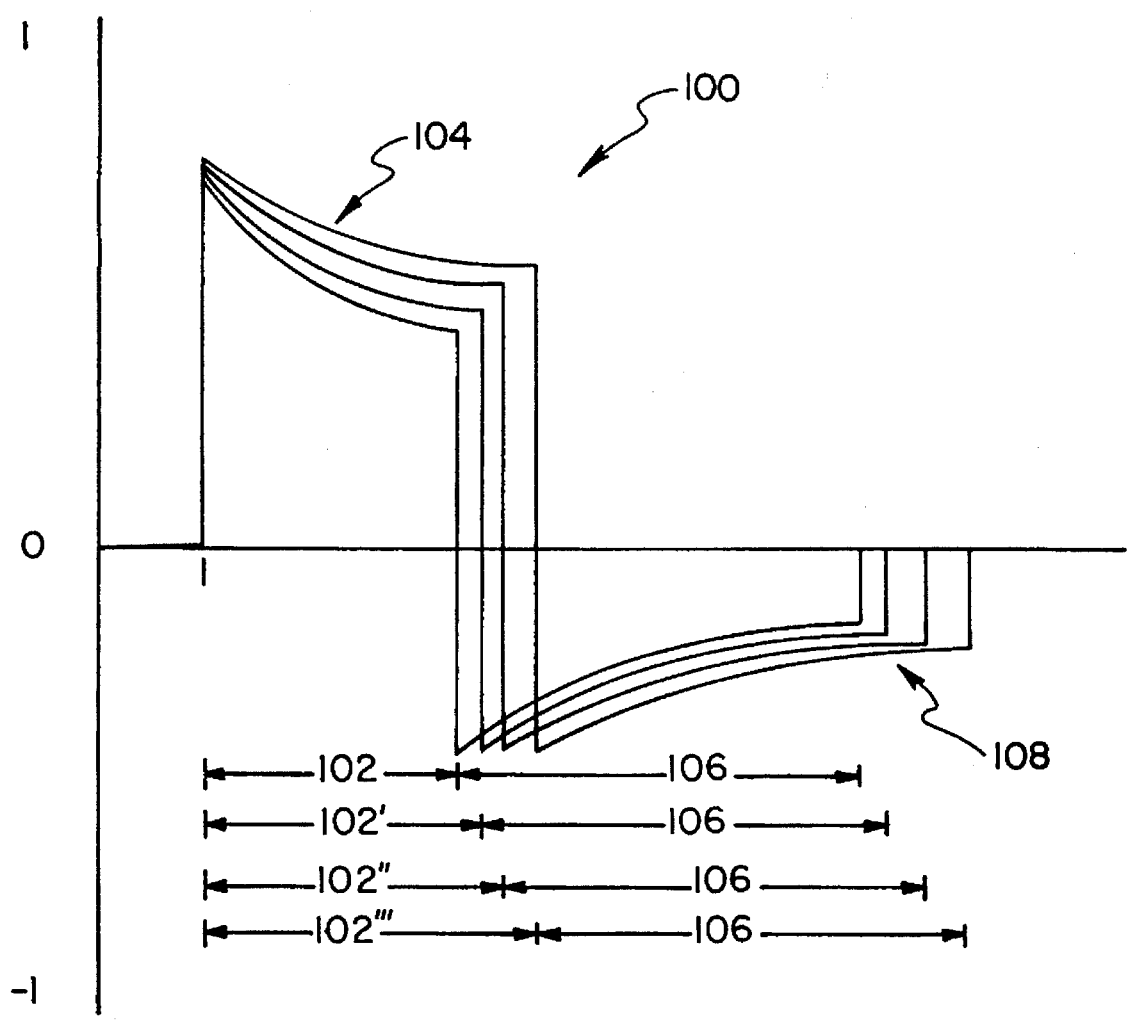
FIG. 10 shows a graph of the output voltages for biphasic waveforms produced in accordance with the present invention.

Referring now to FIG. 9, a simplified circuit diagram of a preferred embodiment of circuitry 60 is used to produce the variable duration first phase, fixed duration second phase biphasic waveforms 100 as shown in FIG. 10. Battery system 62 activates a primary winding on flyback split winding transformer 64 when switch 66 is activated at a high frequency by oscillator 68 within controller 70. The secondary winding of transformer 64 charges a capacitor system 72 through diode 74. Electrodes 40 and 42 about heart 44, as well as switches 34, 35, 36 and 37 may be similar to those used in circuitry 20 as described in connection with FIG. 2. A resistor divider network 76 include a tap 78 which is used to dynamically measure the output voltage across electrodes 40 and 42 and provide that to a comparator within 80 within controller 70. The other input to comparator 80 is provided by a microprocessor 82 from a programmable value stored memory 84, both of which are part of controller 70. This output of comparator 80 provides a tilt-based control of a variable duration 102 of first phase 104 of biphasic waveforms 100 as shown in FIG. 10 by controlling when switches 34 and 37 are shut off.

Alternatively, variable duration 102 of first phase 104 may include both a tilt-based variable portion and a fixed portion determined in accordance with an optimum pulse duration for first phase 102 as set forth, for example, in Eq. (21). In this situation, a fixed duration timer 90 is triggered by the output of comparator 80 and the output of duration timer 90 is then used to control when switches 34 and 37 will be shut off. In FIG. 9, a multiplexer 92 under control of microprocessor 82 is used to allow either of these options to be programmably selected to determine the manner in which the variable duration 102 of first phase 104 will be established.

The length of a fixed duration 106 of second phase 108 of biphasic waveforms 100 as shown in FIG. 10 is established by a duration timer 94 which is triggered either by comparator 80 through multiplexer 92 or by duration timer 90, depending upon which variable duration technique was used to establish the duration of first phase 104. When duration timer 94 expires, switches 35 and 36 are shut off, thereby ending delivery of biphasic waveform 100.

It will be appreciated by those skilled in the art that duration timers 90 and 94 may be programmably loaded with fixed values under control of microprocessor 82 from values stored in memory 84. Alternatively, microprocessor 82 may be in communication with an external programming device (not shown) via antenna 96 to either directly load the fixed values for duration timers 90 and 94 or alter the values stored in memory 84. It will also be appreciated by those skilled in the art that the functions accomplished by controller 70 could be accomplished by alternative arrangements, such as by providing for a hardwired control system, rather than a microprocessor 82 and associated firmware or software, for example. In another example, an analog-to-digital converter could be used to sample the output voltage across electrodes 40 and 42 to form the basis on which a digital comparison would be made, for example, within microprocessor 82 to determine the output condition which would trigger the end of all or a portion of first phase 104.

In still another embodiment, the interelectrode resistance between electrodes 40 and 42 could be dynamically measured (e.g., by calculating the resistance of a known sampling pulse prior to delivery of the countershock) could be used to establish the variable duration of first phase 104. In a preferred embodiment for this technique, the intereelectrode resistance is dynamically determined by measuring the duration of the first subportion (i.e., the tilt-based portion) of first phase 104. using this duration, it is possible to dynamically calculate the interelectrode resistance as seen by the first phase of the biphasic countershock. This resistance value can then be used to calculate the optimal duration of the second phase during delivery of the second subportion of the first phase, such as by direct solution or by using a look up table. Other arrangements of the control of duration timers 90 and 92 could also be provided.

We claim:

1. An implantable defibrillator apparatus electrically connected to at least two electrodes adapted for implantation in a human patient to treat cardiac dysrhythmia by delivering a biphasic countershock, the implantable defibrillator apparatus comprising:

an implantable housing which contains:
sensing means for sensing a cardiac dysrhythmia in the human patient;
capacitor means for storing an electrical charge;
source means for charging the capacitor means to a charging voltage; and
control means for selectively controlling the power source means and the capacitive charge storage means in response to the sensing of the cardiac dysrhythmia to deliver a biphasic countershock to the at least two electrodes including:
means for controlling a first duration of a first phase of the biphasic countershock that has a first polarity such that the first duration is variable; and
means for controlling a second duration of a second phase of the biphasic countershock that has a second polarity that is opposite from the first polarity such that the second duration is fixed.

2. The implantable defibrillator apparatus of claim 1 wherein the means for controlling the first duration dynamically determines a first portion of the first duration based upon a measured tilt of an output voltage of the electrical charge and determines a second portion of the first duration based on a predetermined time value.

3. The implantable defibrillator apparatus of claim 2 wherein the means for controlling the first duration uses a percentage of a system time constant for the implantable defibrillator system to determine the first portion of the first duration and uses a percentage of a predetermined human chronaxie value to determine the second portion of the first duration.

4. The implantable defibrillator apparatus of claim 1 wherein the means for controlling the first duration includes means for dynamically measuring a resistance value across the at least two electrodes that is used to variably control the first duration for the first phase.

5. The implantable defibrillator apparatus of claim 1 wherein the means for controlling the second duration programmably establishes the second duration at a fixed value between 2 to 4 milliseconds.

6. The implantable defibrillator apparatus of claim 1 wherein the means for controlling the second duration is preset to establish the second duration at a constant value of about 2.5 milliseconds.

7. The implantable defibrillator apparatus of claim 1 wherein the control means communicates with a programming device external to the human patient to programmably establish at least one programmable value selected from the set comprising: a tilt value for the first duration, a tilt value and a fixed value for the first duration, a fixed value for the second duration and any combination thereof.

8. An improved implantable defibrillator system for producing a biphasic capacitive-discharge countershock to be delivered through at least two electrodes adapted for implantation in a human patient, the implantable defibrillator system being a self-contained human implantable housing containing a waveform-generating capacitor means for storing an electrical charge, means for charging the waveform-generating capacitor means, and means for selectively discharging the electrical charge in the waveform-generating capacitor means as a biphasic countershock to be delivered through the at least two electrodes in response to a means for sensing of a cardiac dysrhythmia in the human patient, the improvement comprising:

the means for selectively discharging including:
means for controlling a first duration of a first phase of the biphasic countershock such that the discharge of the electrical charge is of a first polarity and the first duration is variable and increases with an increase of a system time constant for the implantable defibrillator system; and
means for controlling a second duration of a second phase of the biphasic countershock such that the discharge of the electrical charge is of a second polarity that is opposite from the first polarity and the second duration is variable and decreases with an increase of the system time constant for the implantable defibrillator system.

9. The implantable defibrillator system of claim 8 wherein the system time constant is less than about 2 milliseconds.

10. The implantable defibrillator system of claim 8 wherein an effective capacitance of the waveform generating capacitor means is less than about 80 μF and an interelectrode resistance between the at least two electrodes is greater than about 25 Ω.

11. The implantable defibrillator system of claim 8 wherein the means for controlling the second duration determines an optimal second duration ($d_2$) by solution of the equation:

$$d_2(opt)=[(\tau_s\tau_m)/(\tau_s-\tau_m)]ln[2-(e^{-d_1/\tau_m}/e^{-d_1/\tau_s})],$$

where ($d_1$) is the first duration of the first phase of the biphasic waveform, $\tau_s$ is the system time constant for the implantable defibrillator system and $\tau_m$ is a system time constant for a heart cell membrane.

12. The implantable defibrillator system of claim 11 wherein solutions for the equation for the optimal second duration are precalculated for a range of values for $d_1$, $\tau_s$, and $\tau_m$ and stored in a memory in the implantable defibrillator, and wherein the means for controlling the second duration selectively chooses among the stored solutions based on determined values for at least $d_1$ and $\tau_s$.

13. The implantable defibrillator system of claim 8 wherein the means for controlling the second duration dynamically determines an interelectrode resistance value between the at least two electrodes and uses the interelectrode resistance value to determine an optimal value for the second duration.

14. The implantable defibrillator system of claim 8 wherein the means for controlling the first duration discharges a first portion of the electrical charge based upon a measured tilt of an output voltage of the electrical charge and discharges a second portion of the electrical charge based on a predetermined time value.

15. The implantable defibrillator system of claim 14 wherein the means for controlling the second duration dynamically determines an interelectrode resistance value between the at least two electrodes based on a measured duration of the first portion and uses the interelectrode resistance value to determine an optimal value for the second duration.

16. The implantable defibrillator system of claim 15 wherein the means for controlling the second duration determines the optimal second duration ($d_2$) by solution of the equation:

$$d_2(opt)=[(\tau_s\tau_m)/(\tau_s-\tau_m)]ln[2-(e^{-d_1/\tau_m}/e^{-d_1/\tau_s})],$$

where ($d_1$) is the first duration of the first phase of the biphasic waveform, $\tau_s$ is the system time constant for the implantable defibrillator system and $\tau_m$ is a system time constant for a heart cell membrane.

17. An improved implantable defibrillator system for producing a biphasic capacitive-discharge countershock to be delivered through at least two electrodes adapted for implantation in a human patient, the implantable defibrillator system being a self-contained human implantable housing containing a waveform-generating capacitor means for storing an electrical charge, means for charging the waveform-generating capacitor means, and means for selectively discharging the electrical charge in the waveform-generating capacitor means as a biphasic countershock to be delivered through the at least two electrodes in response to a means for sensing of a cardiac dysrhythmia in the human patient, the improvement comprising:

the means for selectively discharging including:

means for controlling a first duration of a first phase of the biphasic countershock such that the discharge of the electrical charge is of a first polarity and the first duration is variable; and means for controlling a second duration of a second phase of the biphasic countershock such that the discharge of the electrical charge is of a second polarity that is opposite from the first polarity and the second duration is fixed.

18. The implantable defibrillator system of claim 17 wherein the means for controlling the first duration discharges a first portion of the electrical charge based upon a measured tilt of an output voltage of the electrical charge and discharges a second portion of the electrical charge based on a predetermined time value.

19. The implantable defibrillator system of claim 18 wherein the means for controlling the first duration uses a percentage of a system time constant for the implantable defibrillator system to determine the first portion of the discharge and uses a percentage of a predetermined human chronaxie value to determine the second portion of the discharge.

20. The implantable defibrillator system of claim 17 wherein the means for controlling the first duration includes means for dynamically measures a resistance value across the at least two electrodes that is used to variably control the first duration for the first phase.

21. The implantable defibrillator system of claim 17 wherein the means for controlling the second duration programmably establishes the second duration at a fixed value between 2 to 4 milliseconds.

22. The implantable defibrillator system of claim 17 wherein the means for controlling the second duration is preset to establish the second duration at a constant value of about 2.5 milliseconds.

23. The implantable defibrillator system of claim 17 wherein the means for selectively discharging communicates with a programming device external to the human patient to programmably establish at least one programmable value selected from the set comprising: a tilt value for the first duration, a tilt value and a fixed value for the first duration, a fixed value for the second duration and any combination thereof.

24. A method for operating an implantable defibrillator device electrically connected to at least two electrodes adapted for implantation in a human patient to treat cardiac dysrhythmia by delivering a biphasic countershock, the method comprising the device-implemented steps of:

(a) sensing for a cardiac dysrhythmia in a human patient;

(b) in response to sensing the cardiac dysrhythmia, charging a capacitive charge storage system within the implantable defibrillator device to a charge value;

(c) selectively discharging at least a first portion of the charge value stored in the capacitive charge storage system through the at least two electrodes to produce a first phase of the biphasic countershock, the first phase having a first polarity and a first duration that is variable; and (d) discharging at least a second portion of the charge value stored in the capacitive charge storage system through the at least two electrodes to produce a second phase of the biphasic countershock, the second phase having a second polarity that is opposite from the first polarity and having a second duration that is fixed.

25. The method of claim 24 wherein step (c) comprises:

(c1) discharging a first subportion of the first portion of the charge value based upon a measured tilt of an output voltage of the electrical charge; and (c2) discharging and second subportion of the first portion of the charge value based on a predetermined time value.

26. The method of claim 25 wherein step (c1) uses a percentage of a system time constant for the implantable defibrillator system to determine the first portion of the charge value, and wherein step (c2) uses a percentage of a predetermined human chronaxie value to determine the second portion of the charge value.

27. The method of claim 26 wherein step (c) further includes the step of dynamically measuring a resistance value across the at least two electrodes that is used to variably control the first duration for the first phase.

28. The method of claim 24 wherein step (d) further includes the step of programmably establishing the second duration at a fixed value between 2 to 4 milliseconds.

29. The method of claim 24 wherein step (d) is accomplished by fixing the second duration at a constant value of about 2.5 milliseconds.

30. The method of claim 24 further comprising the step of:

(e) communicating with a programming device external to the human patient to programmably establish at least one programmable value selected from the set comprising: a tilt value for the first duration, a tilt value and a fixed value for the first duration, a fixed value for the second duration and any combination thereof.

* * * * *